United States Patent
Yamaguchi

(10) Patent No.: US 10,694,933 B2
(45) Date of Patent: Jun. 30, 2020

(54) IMAGE PROCESSING APPARATUS AND IMAGE PROCESSING METHOD FOR IMAGE DISPLAY INCLUDING DETERMINING POSITION OF SUPERIMPOSED ZOOMED IMAGE

(71) Applicant: SONY CORPORATION, Tokyo (JP)

(72) Inventor: Kenta Yamaguchi, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 648 days.

(21) Appl. No.: 15/306,943

(22) PCT Filed: Jun. 1, 2015

(86) PCT No.: PCT/JP2015/002752
§ 371 (c)(1),
(2) Date: Oct. 26, 2016

(87) PCT Pub. No.: WO2015/186339
PCT Pub. Date: Dec. 10, 2015

(65) Prior Publication Data
US 2017/0046842 A1 Feb. 16, 2017

(30) Foreign Application Priority Data
Jun. 4, 2014 (JP) .................................. 2014-115768

(51) Int. Cl.
*A61B 1/00* (2006.01)
*A61B 90/20* (2016.01)
(Continued)

(52) U.S. Cl.
CPC .......... *A61B 1/3132* (2013.01); *A61B 1/0005* (2013.01); *A61B 1/00009* (2013.01);
(Continued)

(58) Field of Classification Search
CPC ............ A61B 1/00009; A61B 1/00193; A61B 1/0005; A61B 2034/2005; A61B 5/7425;
(Continued)

(56) References Cited

U.S. PATENT DOCUMENTS 6,036,637 A * 3/2000 Kudo ................. A61B 1/00039
600/102
9,332,242 B2 * 5/2016 Adler ..................... H04N 13/10
(Continued)

FOREIGN PATENT DOCUMENTS

EP 1 944 733 A2 7/2008
JP 5-115432 A 5/1993
(Continued)

OTHER PUBLICATIONS

Office Action dated Jan. 3, 2019 in European Patent Application No. 15728187.4, citing document AO therein, 4 pages.
(Continued)

*Primary Examiner* — John P Leubecker
(74) *Attorney, Agent, or Firm* — Xsensus LLP

(57) ABSTRACT

A medical imaging apparatus including a controller including circuitry configured to control display on a display area of a medical image, control display on the display area of a superimposed image corresponding to the medical image such that the superimposed image is displayed overlapped on the medical image, detect a position of an important element within the medical image, and determine a position of the superimposed image within the display area, based on the detected position of the important element, such that the superimposed image does not overlap on the important element within the medical image.

14 Claims, 20 Drawing Sheets

(51) Int. Cl.
  *G06T 7/00* (2017.01)
  *A61B 1/313* (2006.01)
  *G06T 7/73* (2017.01)
  *A61B 34/20* (2016.01)
  *A61B 90/00* (2016.01)

(52) U.S. Cl.
  CPC ............ *A61B 90/20* (2016.02); *G06T 7/0012* (2013.01); *G06T 7/73* (2017.01); *A61B 2034/2057* (2016.02); *A61B 2034/2065* (2016.02); *A61B 2090/373* (2016.02); *G06T 2207/10012* (2013.01); *G06T 2207/10056* (2013.01); *G06T 2207/10068* (2013.01); *G06T 2207/30004* (2013.01)

(58) Field of Classification Search
  CPC .............. A61B 5/743; A61B 2090/364; A61B 2090/365; A61B 90/37
  See application file for complete search history.

(56) References Cited

U.S. PATENT DOCUMENTS

| | | | |
|---|---|---|---|
| 2003/0069471 | A1 | 4/2003 | Nakanishi et al. |
| 2006/0281971 | A1* | 12/2006 | Sauer ............... A61B 34/20 600/109 |
| 2008/0004603 | A1* | 1/2008 | Larkin ............... B25J 9/1692 606/1 |
| 2008/0137942 | A1* | 6/2008 | Hong ............... H04N 1/62 382/164 |
| 2010/0128116 | A1* | 5/2010 | Sato ............... A61B 1/00045 348/65 |
| 2011/0221866 | A1 | 9/2011 | Ohta |
| 2012/0133670 | A1* | 5/2012 | Kim ............... G09G 5/02 345/593 |
| 2012/0209123 | A1* | 8/2012 | King ............... A61B 5/7485 600/476 |
| 2013/0023730 | A1* | 1/2013 | Kitamura ............ A61B 1/00009 600/104 |
| 2013/0104066 | A1 | 4/2013 | Soederstroem |
| 2013/0195337 | A1 | 8/2013 | Sakagawa |
| 2014/0051986 | A1 | 2/2014 | Zhao et al. |
| 2014/0104684 | A1 | 4/2014 | Ohta |
| 2015/0077529 | A1* | 3/2015 | Hatta ............... A61B 1/00009 348/54 |
| 2015/0235373 | A1* | 8/2015 | Kato ............... A61B 1/00009 348/51 |
| 2015/0363979 | A1* | 12/2015 | Takano ............... A61B 6/461 345/633 |
| 2017/0105809 | A1* | 4/2017 | Kruger ............... A61B 90/36 |

FOREIGN PATENT DOCUMENTS

| | | |
|---|---|---|
| JP | 6-319695 A | 11/1994 |
| JP | 7-154687 A | 6/1995 |
| JP | 9-28663 A | 2/1997 |
| JP | 2001-299742 A | 10/2001 |
| JP | 2003-84201 A | 3/2003 |
| JP | 2010-154957 A | 7/2010 |
| JP | 2012-75508 A | 4/2012 |
| JP | 2012-235983 A | 12/2012 |
| JP | 2012-245157 A | 12/2012 |
| JP | 5297541 B2 | 9/2013 |
| WO | WO 2014/028394 A1 | 2/2014 |

OTHER PUBLICATIONS

International Search Report dated Aug. 7, 2015 in corresponding PCT/JP2015/002752 citing documents AA, AB, AC, AD, AE, AF, AS, AT, AU and AV therein, 3 pages.

Combined Chinese Office Action and Search Report dated Oct. 23, 2017 in corresponding Patent Application No. 201580027803.9 (with English Translation) citing documents AA, AB, AS, AU and AV therein, 14 pages.

Office Action dated Nov. 30, 2017 in corresponding Japanese Patent Application No. 2014-115768, 6 pages.

* cited by examiner

IMAGE PROCESSING APPARATUS AND IMAGE PROCESSING METHOD FOR IMAGE DISPLAY INCLUDING DETERMINING POSITION OF SUPERIMPOSED ZOOMED IMAGE

TECHNICAL FIELD

The present disclosure relates to an image processing apparatus and an image processing method, particularly, to an image processing apparatus and an image processing method allowed to display a surgery region desired by a practitioner without an effort of the practitioner.

CROSS REFERENCE TO RELATED APPLICATIONS

This application claims the benefit of Japanese Priority Patent Application JP 2014-115768 filed Jun. 4, 2014, the entire contents of which are incorporated herein by reference.

BACKGROUND ART

An endoscopic surgery has been used in which an endoscope is inserted into a body, a region (surgery region) being a surgical target in the body is captured as an observed portion to display the captured region on a screen by using the endoscope, and treatment is performed on the surgery region while viewing the screen. In the endoscopic surgery, desired signal processing is performed on an image signal of the observed portion which has an optical image and is obtained in the endoscope by applying illumination light to the observed portion from a light source device and an image of the observed portion having an optical image is displayed on a screen.

In such an endoscopic surgery, it is necessary that a range or a position of an observed portion to be displayed on the screen is appropriately adjusted depending on circumstances in order for a practitioner performing surgery to ensure an optimal view field (surgical field) for a surgery region.

However, typically, the practitioner holds a surgical instrument for performing surgery with both hands. Accordingly, it is difficult for the practitioner to operate a work of such the screen adjustment rapidly for himself. The practitioner operating an adjustment mechanism and the like for himself for screen adjustment is not preferable in view of ensuring a degree of cleanness of a surgery region, medical equipment, an operating room, and the like.

Thus, in general, an instruction of the practitioner is given to an assistant called a scopist or the like and the assistant operates the adjustment mechanism in accordance with the instruction from the practitioner to perform such the screen adjustment.

However, in the method in which the assistant intervenes, the instruction of the practitioner may be transferred inaccurately and thus rapid screen adjustment desired by the practitioner may be difficult.

As a method of adjusting a screen without an assistant intervening, for example, a surgical supporting system in which the practitioner recognizes forceps to adjust expansion or brightness of a camera, has been proposed in PTL 1.

CITATION LIST

Patent Literature

PTL 1: Japanese Unexamined Patent Application Publication No. 2012-65698

SUMMARY OF INVENTION

Technical Problem

However, in the surgical supporting system of PTL 1, it is necessary that the practitioner operates the camera and in order to operate the camera, it is necessary to stop performing surgery.

Considering such circumstances, a region of interest desired by a practitioner can be displayed without an effort of the practitioner in the present disclosure.

Solution to Problem

According to an embodiment of the present disclosure, there is provided a medical imaging apparatus including a controller including circuitry configured to control display on a display area of a medical image, control display on the display area of a superimposed image corresponding to the medical image such that the superimposed image is displayed overlapped on the medical image, detect a position of an important element within the medical image, and determine a position of the superimposed image within the display area, based on the detected position of the important element, such that the superimposed image does not overlap on the important element within the medical image.

According to another embodiment of the present disclosure, there is provided a method for processing a medical image by a medical imaging apparatus including a controller including circuitry. The method includes the steps of controlling display on a display area of a medical image, controlling display on the display area of a superimposed image corresponding to the medical image such that the superimposed image is displayed overlapped on the medical image, detecting, by the circuitry, a position of an important element within the medical image, and determining a position of the superimposed image within the display area, based on the detected position of the important element, such that the superimposed image does not overlap on the important element within the medical image.

According to another embodiment of the present disclosure, there is provided a medical imaging system including a medical imaging device that obtains a medical image and a display device having a display area.

The medical imaging system further includes a controller including circuitry configured to control display on the display area of the display device of the medical image obtained by the medical imaging device, control display on the display area of the display device of a superimposed image corresponding to the medical image such that the superimposed image is displayed overlapped on the medical image, detect a position of an important element within the medical image, and determine a position of the superimposed image within the display area, based on the detected position of the important element, such that the superimposed image does not overlap on the important element within the medical image.

Advantageous Effects of Invention

According to the embodiments of the present disclosure, it is possible to display a region of interest desired by a practitioner without an effort of the practitioner.

The effect described herein is not necessarily limited thereto and may include any effect described in the present disclosure.

DESCRIPTION OF EMBODIMENTS

1. Configuration Example of Endoscope System

Figure 1:
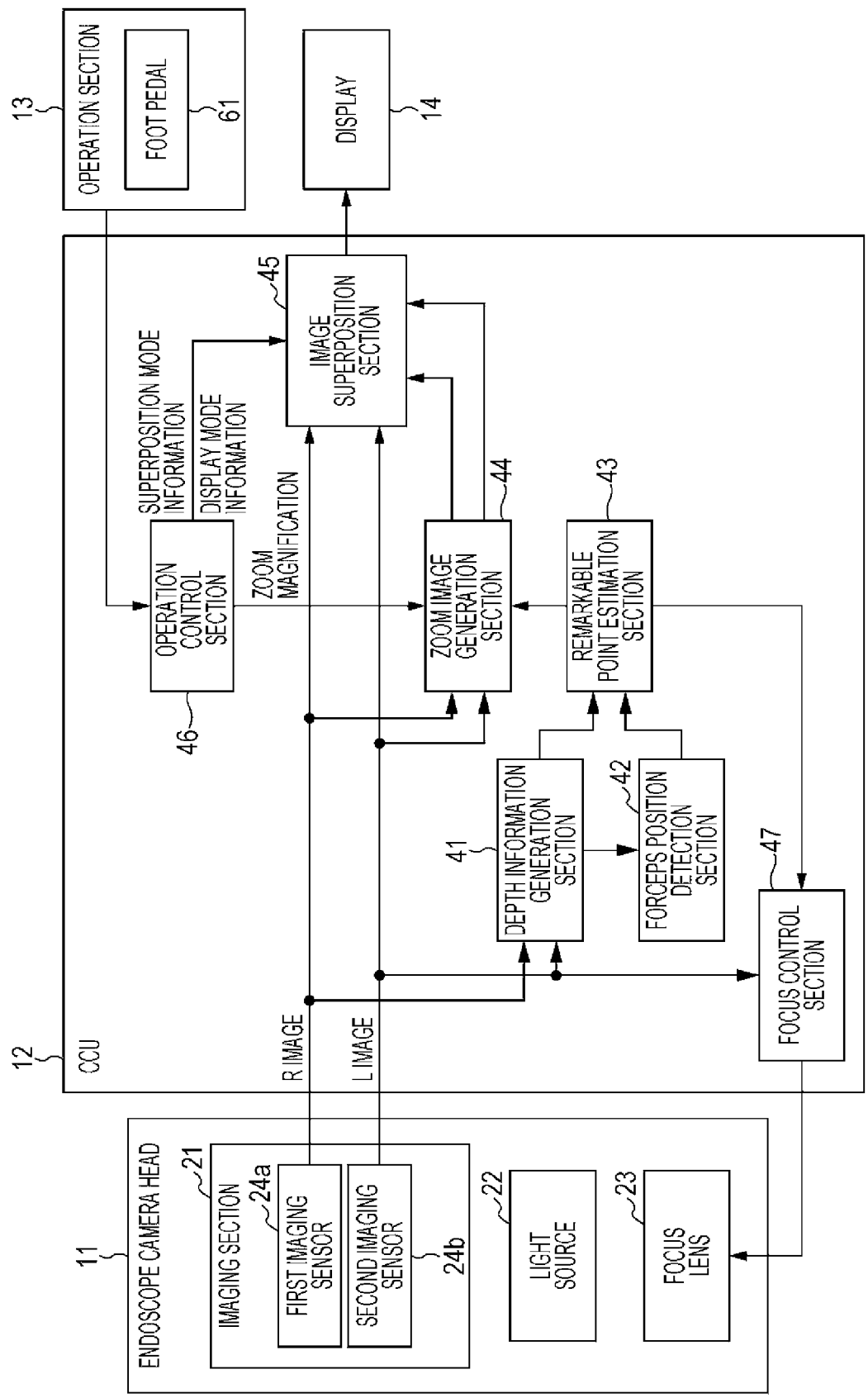
FIG. 1 is a block diagram illustrating a configuration example of an embodiment of an endoscope system according to the present disclosure.

FIG. 1 is a block diagram illustrating a configuration example of an embodiment of an endoscope system according to the present disclosure.

The endoscope system in FIG. 1 is configured by an endoscope camera head 11, a camera control unit (CCU) 12, an operation section 13, and a display 14.

This endoscope system is used in endoscopic surgery in which a region (surgery region) in a body being a surgical target is captured as an observed portion and is displayed on the display 14, and the observed portion is treated while viewing the display 14.

Figure 2:
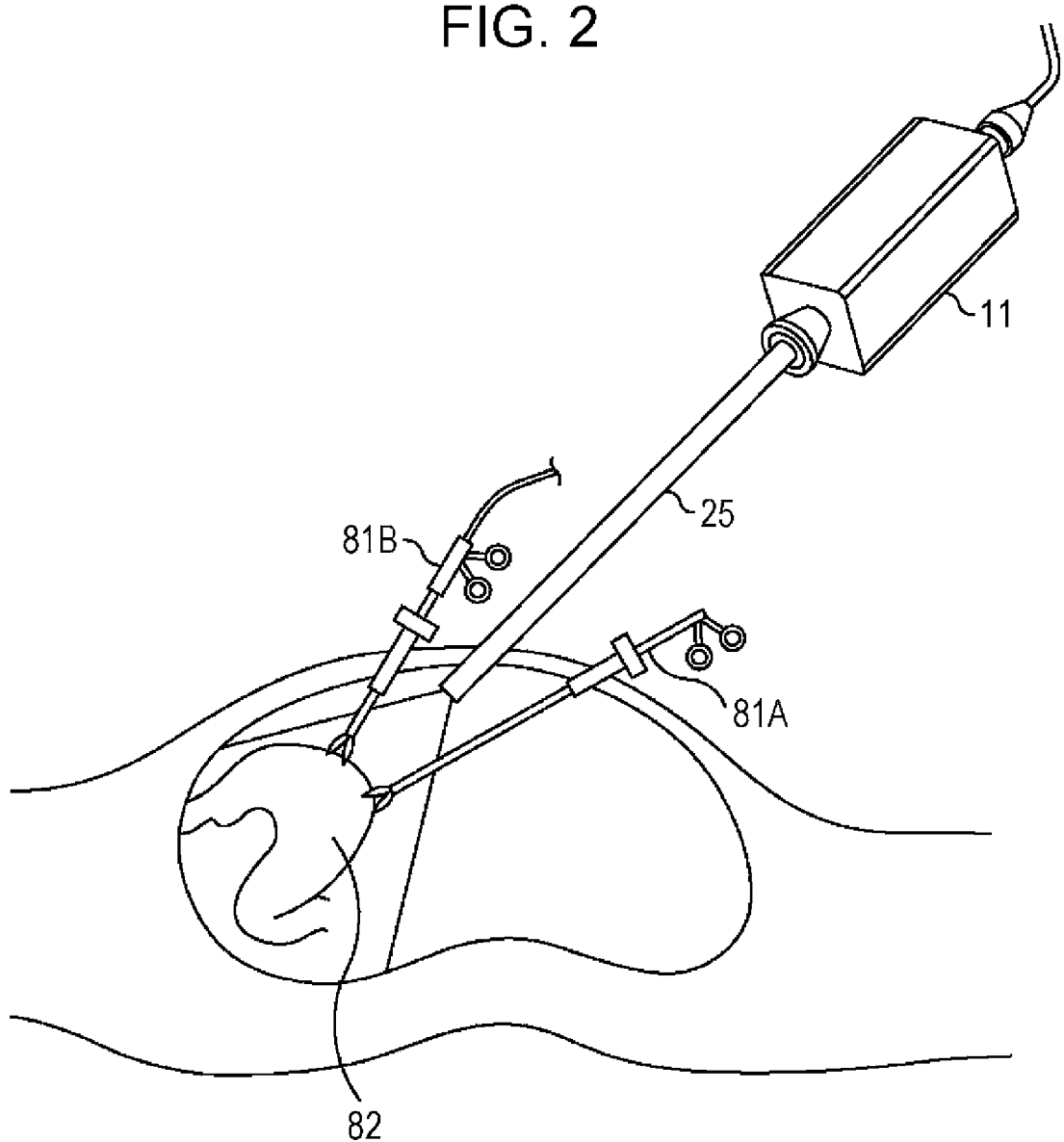
FIG. 2 is a diagram illustrating a usage state of the endoscope system.

In the endoscopic surgery, for example, as illustrated in FIG. 2, an insertion portion 25 of the endoscope camera head 11 and two pairs of forceps 81 (81A and 81B) being surgical instruments are inserted into the body of a patient. The endoscope camera head 11 emits light from a tip end of the insertion portion 25, illuminates a surgery region 82 of the patient, and images a state of the two pairs of forceps 81 and the surgery region 82.

The endoscope camera head 11 includes an imaging section 21, a light source 22, and a focus lens 23, as illustrated in FIG. 1.

The imaging section 21 includes at least two imaging sensors 24 of a first imaging sensor 24a and a second imaging sensor 24b. The imaging sensor 24 is configured by, for example, a charge coupled device (CCD) sensor, a complementary metal oxide semiconductor (CMOS) sensor, or the like. The imaging sensor 24 images a subject and generates an image obtained as a result. The imaging sensor 24 may employ a high resolution sensor which has the number of pixels of about 4000× about 2000 being the number of pixels of (horizontal direction)×(vertical direction) and is called a 4K camera. The two imaging sensors 24 are disposed at a predetermined distance from each other in a traverse direction and generate images having view point directions different from each other to output the images to the CCU 12.

In this embodiment, images obtained by the two imaging sensors 24 performing imaging are referred to as surgery region images. In this embodiment, the first imaging sensor 24a is set to be disposed on a right side and the second imaging sensor 24b is set to be disposed on a left side, and the surgery region image generated by the first imaging sensor 24a is referred to as an R image and the surgery region image generated by the second imaging sensor 24b is referred to as an L image.

The light source 22 is configured by, for example, a halogen lamp, a xenon lamp, a light emitting diode (LED) light source, and the like and the light source 22 emits light for illuminating the surgery region.

The focus lens 23 is configured by one or a plurality of lenses, and is driven by a focus control section 47 (will be described later) of the CCU 12 and forms an image on an imaging surface of the imaging sensor 24 by using incident light (image light) from the subject.

The CCU 12 is an image processing apparatus for processing the surgery region image obtained by the imaging section 21 of the endoscope camera head 11 performing imaging. The CCU 12 is configured by a depth information generation section 41, a forceps position detection section 42, a remarkable point estimation section 43, a zoom image generation section 44, an image superposition section 45, an operation control section 46, and a focus control section 47.

The R image and the L image which are generated and output by the imaging section 21 are supplied to the depth information generation section 41, the zoom image generation section 44, and the image superposition section 45 of the CCU 12. One (for example, L image) of the R image and the L image is also supplied to the focus control section 47.

The depth information generation section 41 generates depth information of the surgery region image from the supplied R image and L image. More specifically, the depth information generation section 41 calculates a position of each pixel of the surgery region image in a depth direction by using the supplied R image and L image and a principle of triangulation.

A calculation method of a depth position of each pixel in the surgery region image will be described by using the principle of triangulation with reference to FIG. 3 and FIG. 4.

Figure 3:
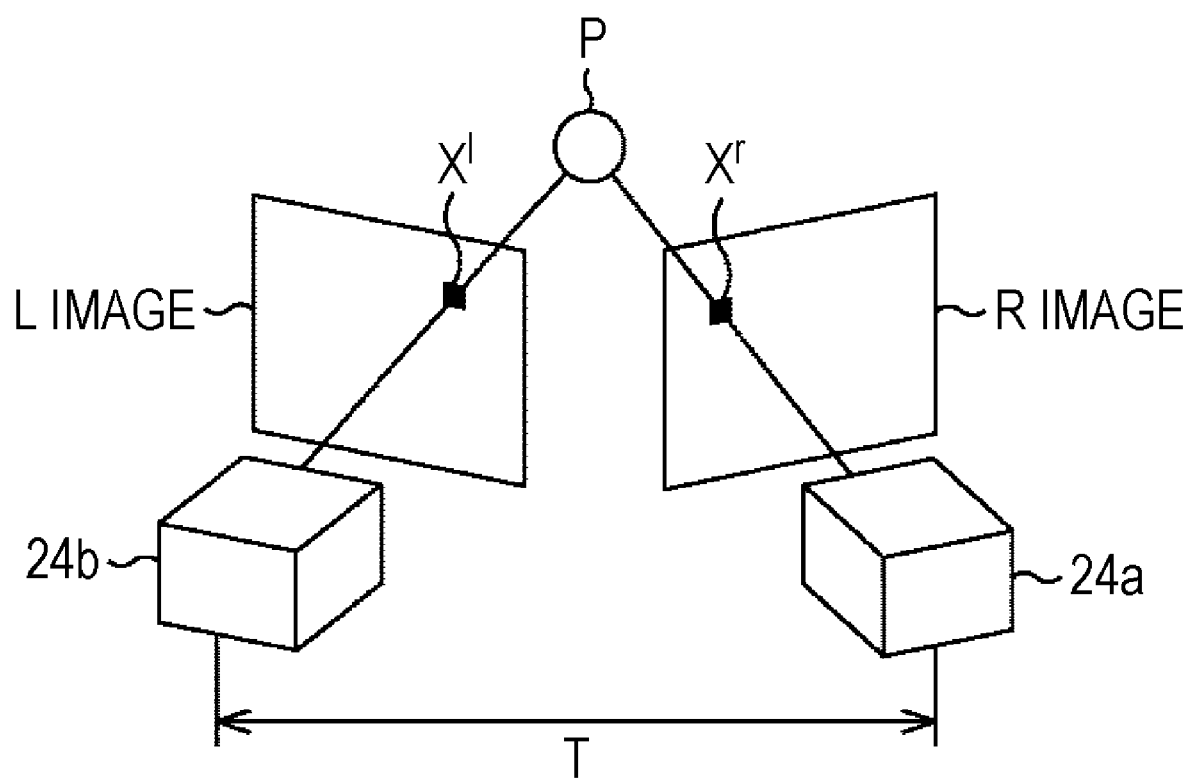
FIG. 3 is a diagram illustrating a calculation method of a depth position.

First, the first imaging sensor 24a and the second imaging sensor 24b are arranged in a row at a distance T in the traverse direction, as illustrated in FIG. 3, and each of the first imaging sensor 24a and the second imaging sensor 24b images an object P in the real world.

The positions of the first imaging sensor 24a and the second imaging sensor 24b in the vertical direction are the same as each other and the positions in the horizontal direction are different from each other. Thus, the position of the object P in the R image obtained by the first imaging sensor 24a and the position of the object P in the L image obtained by the second imaging sensor 24b are different only in x coordinates.

For example, the x coordinate of the object P shown in the R image obtained by the first imaging sensor 24a is set to $x^r$ and the x coordinate of the object P shown in the L image obtained by the second imaging sensor 24b is set to $x^l$.

Figure 4:
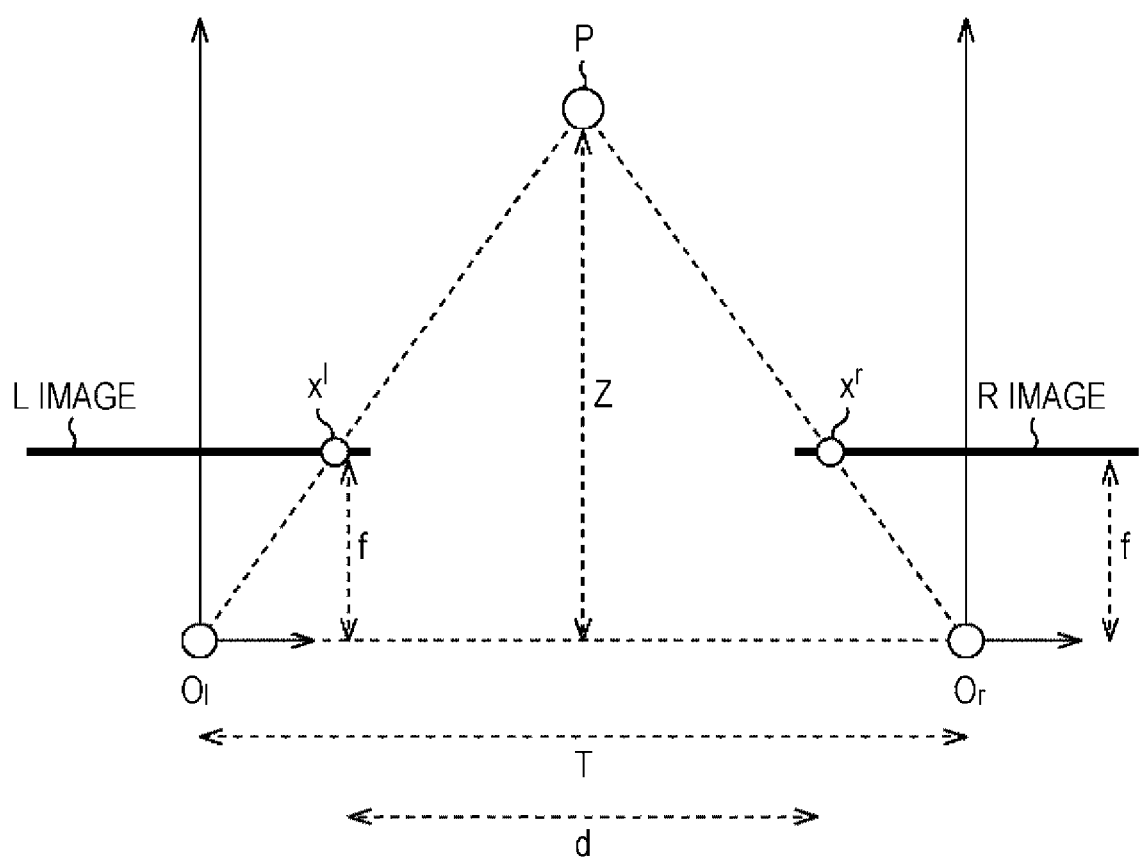
FIG. 4 is a diagram illustrating the calculation method of the depth position.

If the principle of triangulation is used, as illustrated in FIG. 4, the x coordinate of the object P in the R image being $x^r$ corresponds to a position on a straight line joining an optical center $O_r$ of the first imaging sensor 24a and the object P. The x coordinate of the object P in the L image being $x^l$ corresponds to a position on a straight line joining an optical center $O_l$ of the second imaging sensor 24b and the object P.

Here, when a distance from the optical center $O_r$ to an image plane of the R image or from the optical center $O_l$ to an image plane of the L image is set as f and a distance (depth) from the a line joining the optical center $O_r$ and the optical center $O_l$ to the object P in the real world is set as Z, parallax d is represented by $d=(x^l-x^r)$.

A relationship of the Equation (1) is established between T, Z, d, and f.

[Math. 1]

$$\frac{T-d}{Z-f} = \frac{T}{Z} \quad (1)$$

Accordingly, the distance Z to the object P may be obtained by using the following Equation (2) which is obtained by deforming the Equation (1).

[Math. 2]

$$Z = \frac{fT}{x^l - x^r} \quad (2)$$

The depth information generation section 41 in FIG. 1 calculates a depth Z of each pixel in the surgery region image by using the above-described principle of triangulation. The depth Z of each pixel calculated by the depth information generation section 41 is supplied to the remarkable point estimation section 43 and the forceps position detection section 42, as depth information.

The forceps position detection section 42 detects a position of an important object such as the forceps 81 shown in the surgery region image using the depth information of the surgery region image supplied from the depth information generation section 41. As described above, the two pairs of forceps 81 may be imaged as subjects in the surgery region image. However, a position of either of the forceps 81 may be detected. The forceps 81 of which the position is to be detected may be determined in advance or the forceps of which the position is detected more easily than another in the surgery region image may be determined. In addition, the positions of the two pairs of forceps 81 may also be detected.

Position detection of the forceps 81 performed by the forceps position detection section 42 will be described with reference to FIG. 5A to FIG. 5D.

First, the forceps position detection section 42 generates a parallax image from depth information of the surgery region image supplied from the depth information generation section 41. The parallax image refers to an image obtained by representing the depth Z of each pixel being the depth information, in gray scale.

Figure 5A:
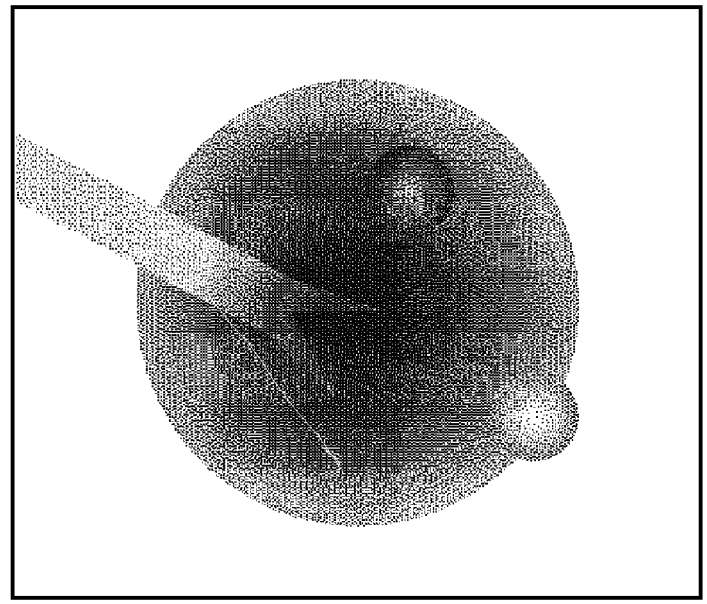
FIG. 5A is a diagram illustrating detection of a position of forceps.

FIG. 5A illustrates an example of the parallax image and represents that brightness value in the parallax image becomes greater, corresponding depth Z becomes less, and the subject in the surgery region image becomes closer to the front.

Then, the forceps position detection section 42 detects an edge which is a boundary between brightness values, from the generated parallax image. For example, pixels which have a difference between pixel values of adjacent pixels is equal to or greater than a predetermined value in the parallax image are detected as an edge.

Figure 5B:
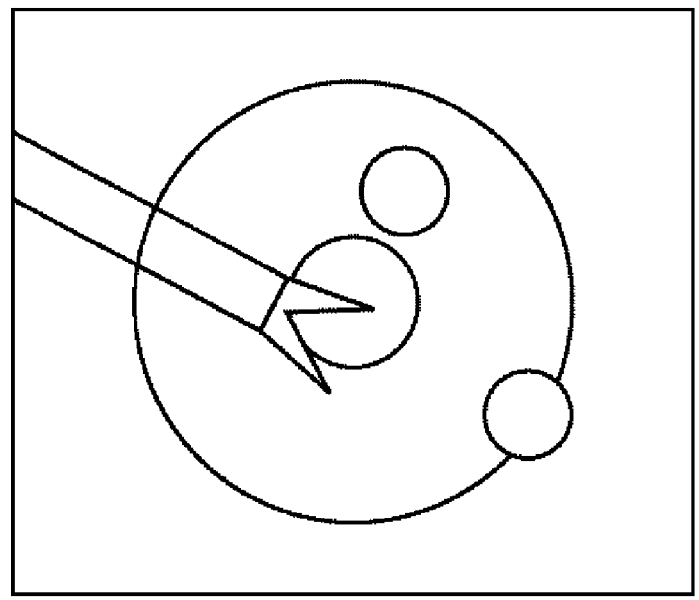
FIG. 5B is a diagram illustrating detection of the position of forceps.
Figure 5C:
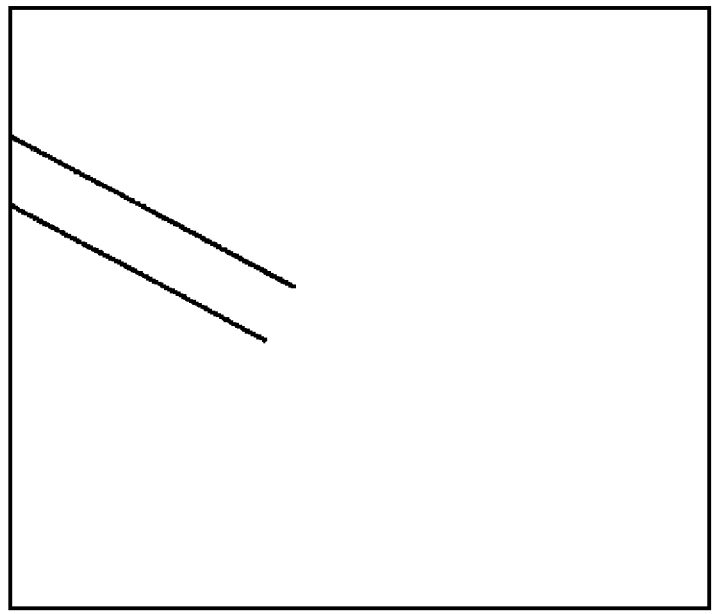
FIG. 5C is a diagram illustrating detection of the position of forceps.

FIG. 5B illustrates an example of the edge detected in the parallax image of FIG. 5A.

In the above-described example, the edge is detected based on the brightness value of the generated parallax image. However, the edge may be detected by using other methods. For example, a main color component at the surgery region in the surgery region image is red, but a color component of the surgical instrument such as the forceps 81 is silver which is a metal-based color, white, or black in many cases. Thus, the forceps position detection section 42 may detect an edge by detecting a region (boundary) of a particular color using color information of the surgery region image.

Then, the forceps position detection section 42 removes a curved edge out of the detected edge and detects only a linear edge having a predetermined length or greater.

Since the forceps 81 has a bar shape, there is the linear edge having a predetermined length or greater, as the edge of the forceps 81. Thus, the forceps position detection section 42 only detects the linear edge having a predetermined length or greater out of the detected edge as the edge of the forceps 81.

The forceps position detection section 42 may determine whether or not the detected linear edge is a straight line continuing from an outer circumference portion of the surgery region image in addition to determining whether or not the detected linear edge has the predetermined length or greater, when the edge of the forceps 81 is specified. When the insertion portion 25 of the endoscope camera head 11 and the forceps 81 have a position relationship as illustrated in FIG. 2, the forceps 81 generally is captured to have a position of being extended to a center portion from the outer circumference portion of the surgery region image in the surgery region image. For this reason, it is possible to further raise detection accuracy of the forceps 81 by determining whether or not the detected linear edge is a straight line continuing from the outer circumference portion of the surgery region image.

Then, the forceps position detection section 42 estimates a position of the forceps 81 in the three-dimensional space in the captured image, that is, a posture of the forceps 81, from the detected linear edge.

Figure 5D:
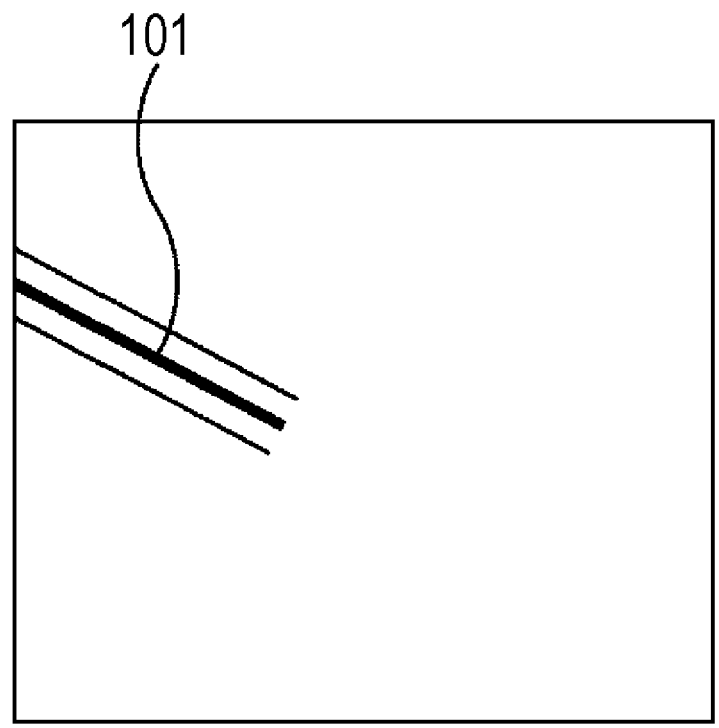
FIG. 5D is a diagram illustrating detection of the position of forceps.

Specifically, the forceps position detection section 42 calculates a line segment (straight line) 101 corresponding to the forceps 81, from the detected linear edge, as illustrated in FIG. 5D. The line segment 101 may be obtained by using an intermediate line between the detected two linear edges, and the like.

The forceps position detection section 42 arbitrarily detects two points $(x_1, y_1)$ and $(x_2, y_2)$ on the calculated line segment 101 and acquires depth positions $z_1$ and $z_2$ at positions $(x_1, y_1)$ and $(x_2, y_2)$ of the detected two points from the supplied depth information. Accordingly, the positions $(x_1, y_1, z_1)$ and $(x_2, y_2, z_2)$ of the forceps 81 in the three-dimensional space are specified in the surgery region image. The positions may include, for example, the distal end of the forceps.

When two line segments corresponding to two pairs of forceps 81 are detected in the surgery region image, either of the two line segments may be selected by selecting one closer to the front than another.

Returning to FIG. 1, the forceps position detection section 42 supplies the positions $(x_1, y_1, z_1)$ and $(x_2, y_2, z_2)$ of the forceps 81 in the three-dimensional space which are detected in the above-described manner, to the remarkable point estimation section 43.

The depth information of the surgery region image is supplied from the depth information generation section 41 to the remarkable point estimation section 43 and the coordinates $(x_1, y_1, z_1)$ and $(x_2, y_2, z_2)$ of the two points in the three-dimensional space which represent a posture of the forceps 81 are supplied from the forceps position detection section 42 to the remarkable point estimation section 43.

Alternatively to the forceps position detection section 42, element 42 can also be an area position detection section. The area position detection section 42 detects an important area having, for example, certain tissues, body parts, bleeding or blood vessels, etc. The detection of the important area is based on color information, brightness and/or differences between different frames. For example, an important area could be detected as an area having no bleeding in one frame and then bleeding in subsequent frames. An important element includes the important object and/or the important area.

Figure 6:
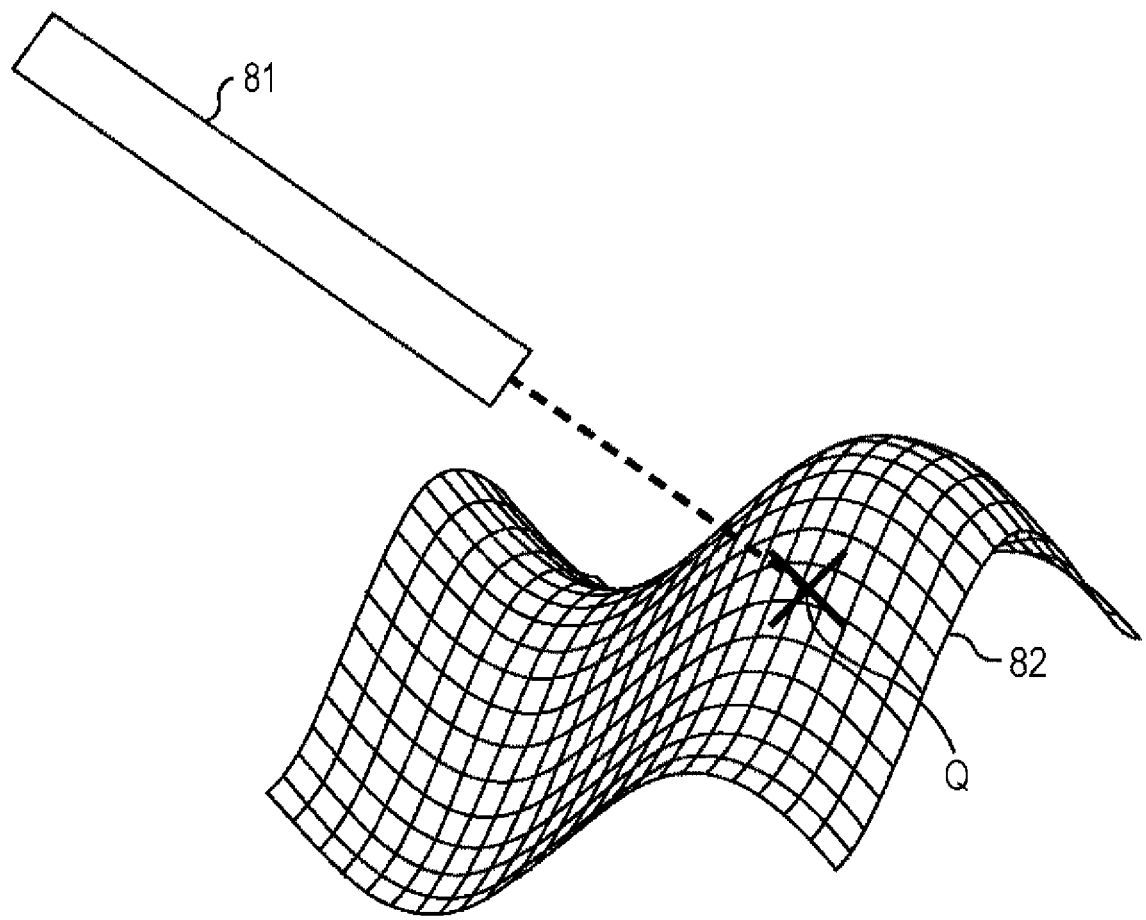
FIG. 6 is a diagram illustrating detection of a position of a remarkable point.

The remarkable point estimation section 43 assumes that a remarkable point Q at the surgery region 82 is at a position obtained by extending the detected positions of the forceps 81 and estimates a position of the remarkable point Q of the surgery region 82 in the three-dimensional space, as illustrated in FIG. 6. The remarkable point Q at the surgery region 82 corresponds to an intersection point of an extension line obtained by extending the detected posture of the forceps 81 and a surface of the surgery region 82. An estimated location coordinate of the remarkable point Q at the surgery region 82 in the three-dimensional space is supplied to the zoom image generation section 44.

The remarkable point estimation section 43 can also estimate the remarkable point Q from the determined important area. In particular, the remarkable point Q can be generated based on the position of the important area.

The zoom image generation section 44 determines a predetermined area having the remarkable point Q supplied from the remarkable point estimation section 43 as the center, as an area of interest in the surgery region image supplied from the imaging section 21. Accordingly, at least the remarkable point Q is included at the area of interest. The zoom image generation section 44 generates a zoom image by expanding an image of the determined area of interest based on a zoom magnification supplied from the operation control section 46 and supplies the generated zoom image to the image superposition section 45.

Superposition mode information which is control information for an instruction of ON or OFF of a superposition mode is supplied to the image superposition section 45 from the operation control section 46. The image superposition section 45 generates a superposition image by superposing the zoom image supplied from the zoom image generation section 44 on a predetermined position of the surgery region image supplied from the imaging section 21 and displays the generated superposition image on the display 14 when an instruction of ON of the superposition mode is received through the superposition mode information.

On the other hand, when an instruction of OFF of the superposition mode is received through the superposition mode information, the image superposition section 45 does not superpose the zoom image but displays only the surgery region image supplied from the imaging section 21 on the display 14.

Display mode information which is control information for an instruction of ON or OFF of 3D display is also supplied to the image superposition section 45 from the operation control section 46. The image superposition section 45 supplies either of the R image and the L image to the display 14 and causes the surgery region image to be displayed in a 2D manner when an instruction of OFF of the 3D display is received through the display mode information. On the other hand, when an instruction of ON of the 3D display is received through the display mode information, the image superposition section 45 supplies both of the R image and the L image to the display 14 and causes the surgery region image to be displayed in a 3D manner. Here, the 3D display refers to an image display manner in which the R image and the L image are alternately displayed on the display 14, the right eye of a practitioner visually recognizes the R image, the left eye of the practitioner visually recognizes the L image, and thus the practitioner perceives the surgery region image three-dimensionally.

The operation control section 46 supplies various control signals to necessary sections based on an operation signal supplied from the operation section 13. For example, the operation control section 46 supplies zoom magnification information for designating predetermined zoom magnification to the zoom image generation section 44 in accordance with a setting operation of zoom magnification performed through the operation section 13. The operation control section 46 supplies the above-described superposition mode information and display mode information to the image superposition section 45.

The focus control section 47 performs focus control by using a contrast method, based on the L image supplied from the imaging section 21. Specifically, the focus control section 47 drives the focus lens 23 of the endoscope camera head 11 and compares contrast of the L image supplied from the imaging section 21 to detect a focus position. The focus control section 47 may perform the focus control in which the location coordinate of the remarkable point Q is acquired from the remarkable point estimation section 43 and an area of a predetermined range having the remarkable point Q as the center is set to be a focus control target area.

The operation section 13 includes at least a foot pedal 61. The operation section 13 receives an operation from a practitioner (operator) and supplies an operation signal corresponding to an operation performed by the practitioner to the operation control section 46. The practitioner may perform, for example, switching the 2D display and the 3D display of the surgery region image displayed on the display 14, switching ON and OFF of superposition display, setting of the zoom magnification of an endoscope, and the like by operating the operation section 13. In this embodiment, switching ON and OFF of the superposition display is performed by pressing the foot pedal 61 down.

The display 14 is configured by, for example, a liquid crystal display (LCD) and the like and displays a surgery region image imaged by the imaging section 21 of the endoscope camera head 11 based on an image signal supplied from the image superposition section 45. When the superposition mode is set to be ON, a superposition image obtained by superposing a zoom image supplied from the zoom image generation section 44 on the surgery region image imaged by the imaging section 21 is displayed on the display 14.

Figure 7:
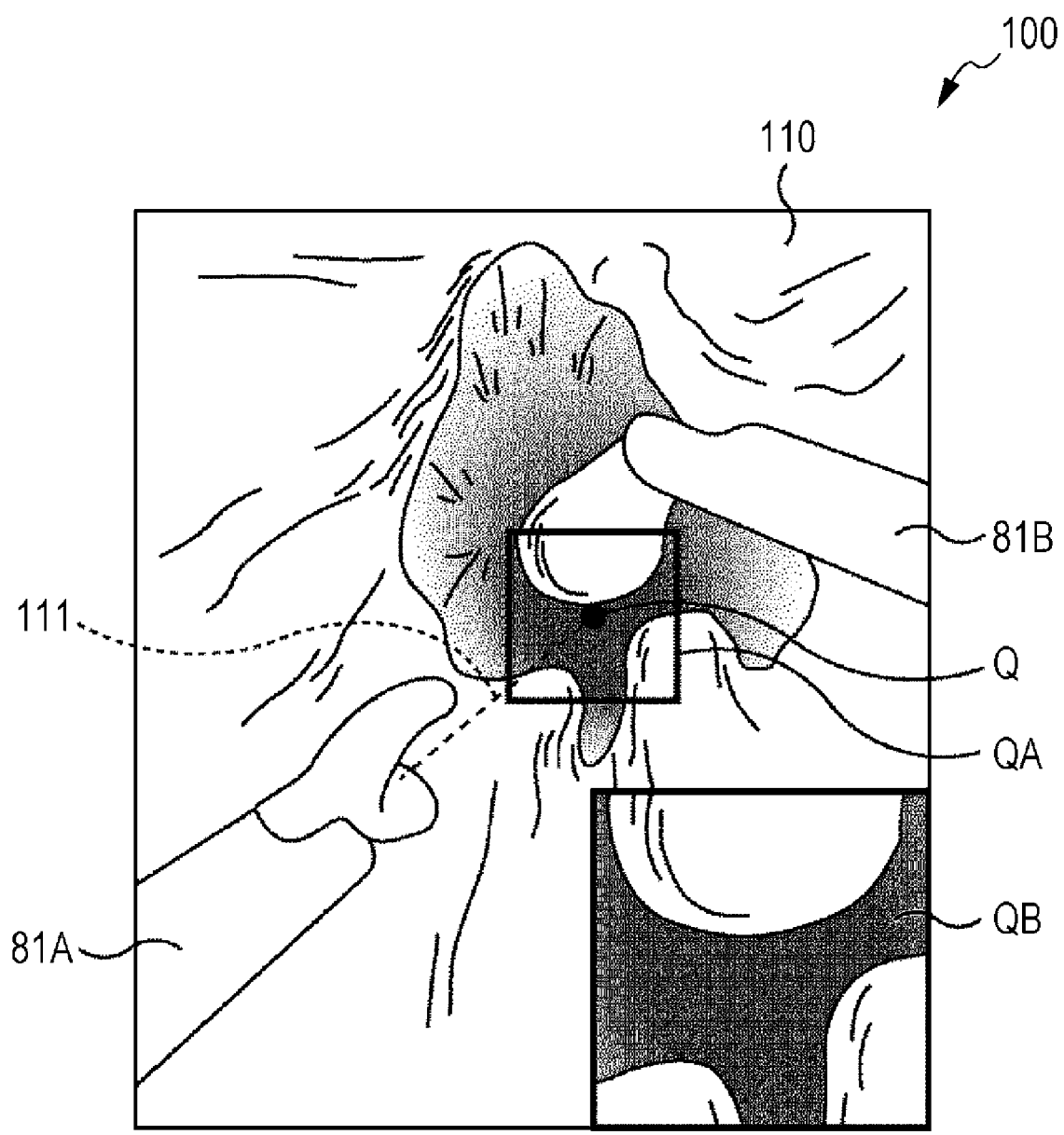
FIG. 7 is a diagram illustrating an example of a superposition image to be displayed on a display.

FIG. 7 illustrates an example of the superposition image displayed on the display 14 when the superposition mode is ON.

In a superposition image 100 of FIG. 7, a zoom image QB is superposed on a surgery region image 110 supplied from the imaging section 21 and the zoom image QB is obtained by expanding an image of an area of interest QA determined based on the remarkable point Q.

In the surgery region image 110, the two pairs of forceps 81A and 81B are imaged and the remarkable point Q is estimated based on a position of the forceps 81A on the left side. In the superposition image 100, the estimated remarkable point Q, the area of interest QA determined based on the remarkable point Q, and a guide line 111 corresponding to an extension line calculated through estimation of the remarkable point Q are displayed. Display of the guide line 111 allows a three-dimensional distance in the abdominal cavity to be recognized visually and intuitively and may cause three-dimensional distance information to be provided for the practitioner in a plan view.

In the example of the superposition image 100 of FIG. 7, the two pairs of forceps 81A and 81B are not included in the area of interest QA. However, the area of interest QA may be determined such that a tip end portion of at least one of the two pairs of forceps 81A and 81B is included in the area of interest QA.

Tip end portions of the two pairs of forceps 81A and 81B are included in the surgery region image 110 of FIG. 7. However, the zoom magnification when the surgery region image 110 is to be obtained may be determined such that the tip end portion of at least one forceps 81 and the remarkable point Q estimated from a posture of the forceps 81 are included in the surgery region image 110.

The example of FIG. 7 is an example in which the zoom image QB is superposed on the lower right of the screen. However, the zoom image QB is disposed appropriately at a position at which the practitioner performing surgery is not disturbed, depending on the position of the forceps 81 or the area of interest QA, as will be described later.

2. Processing Flow of Superposition Displaying Process

A superposition display process performed when the superposition mode is set to be ON in the endoscope system of FIG. 1 will be described. A practitioner can switch ON and OFF of the superposition mode by using the foot pedal 61, for example.

Figure 8:
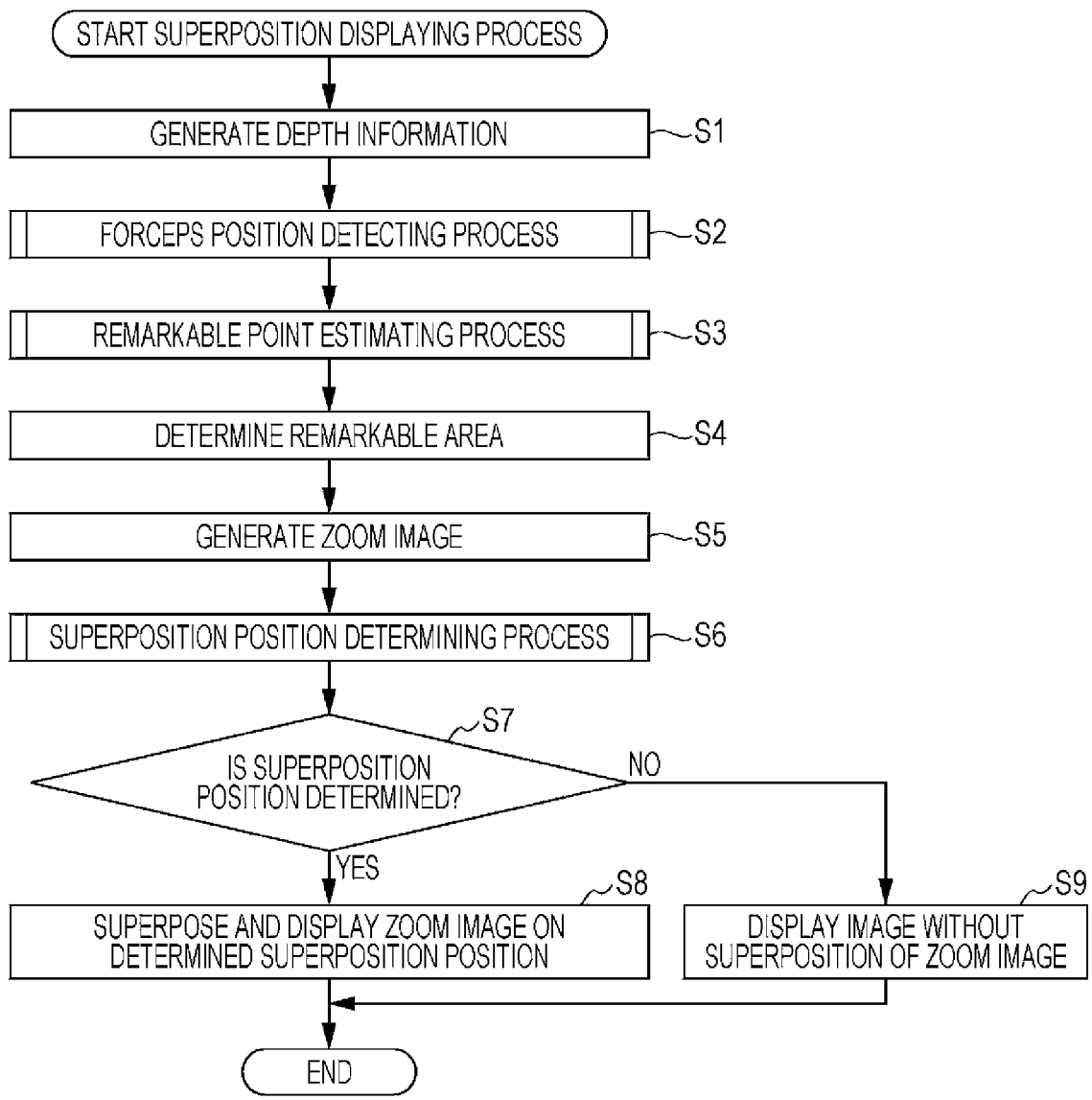
FIG. 8 is a flowchart illustrating a superposition displaying process.

FIG. 8 illustrates a flowchart of the superposition displaying process. Power is supplied to each mechanism of the endoscope system in a state where the superposition displaying process of FIG. 8 is executed. The insertion portion 25 of the endoscope camera head 11 and the forceps 81 are inserted into the body of a patient and the light source 22 illuminates the surgery region 82 of the patient.

First, in Step S1, the depth information generation section 41 generates depth information of a surgery region image from an R image and an L image supplied from the imaging section 21 of the endoscope camera head 11. More specifically, the depth information generation section 41 calculates depth Z of the each location (pixel) in the surgery region image by using the Equation (2) which uses the principle of triangulation described with reference to FIG. 4. Depth information calculated in the depth information generation section 41 is supplied to the remarkable point estimation section 43 and the forceps position detection section 42.

In Step S2, the forceps position detection section 42 executes a forceps position detecting process of detecting a position of the forceps 81 in the surgery region image using the depth information of the surgery region image supplied from the depth information generation section 41. Step S2 can alternatively correspond to the area position detection section 42 executing an area position detecting process.

<Detailed Flow of Forceps Position Detecting Process>

Figure 9:
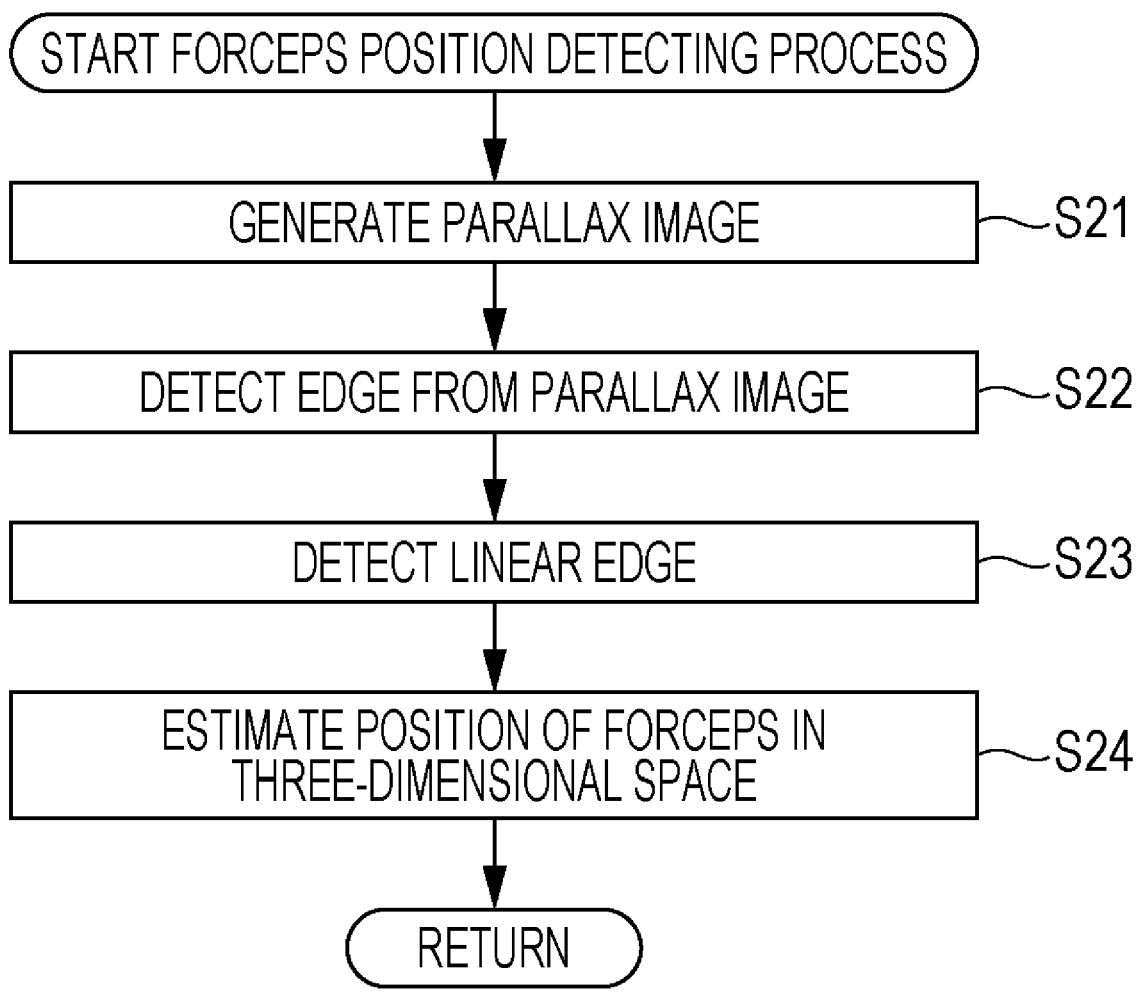
FIG. 9 is a flowchart illustrating a forceps position detecting process in detail.

FIG. 9 illustrates a detailed flowchart of the forceps position detecting process executed in Step S2.

In the forceps position detecting process, at first, in Step S21, the forceps position detection section 42 generates a parallax image from the depth information of the surgery region image supplied from the depth information generation section 41.

In Step S22, the forceps position detection section 42 detects an edge which is a boundary between brightness values from the generated parallax image.

In Step S23, the forceps position detection section 42 removes a curved edge out of the detected edge and detects only a linear edge having a predetermined length or greater.

In Step S24, the forceps position detection section 42 estimates a position of the forceps 81 in the surgery region image in the three-dimensional space from the detected linear edge. With this, as described above with reference to FIG. 5D, coordinates $(x_1, y_1, z_1)$ and $(x_2, y_2, z_2)$ of two points indicating positions of the forceps 81 in the surgery region image in the three-dimensional space are determined.

The positions $(x_1, y_1, z_1)$ and $(x_2, y_2, z_2)$ of the forceps 81 in the surgery region image, which are detected as described above, are supplied to the remarkable point estimation section 43 and the process proceeds to Step S3 in FIG. 8.

In Step S3, the remarkable point estimation section 43 executes a remarkable point estimating process of assuming that a remarkable point Q at the surgery region 82 is at a position obtained by extending the detected positions of the forceps 81 and of detecting a position of the remarkable point Q of the surgery region 82 in the three-dimensional space.

<Detailed Flow of Remarkable Point Estimating Process>

Figure 10:
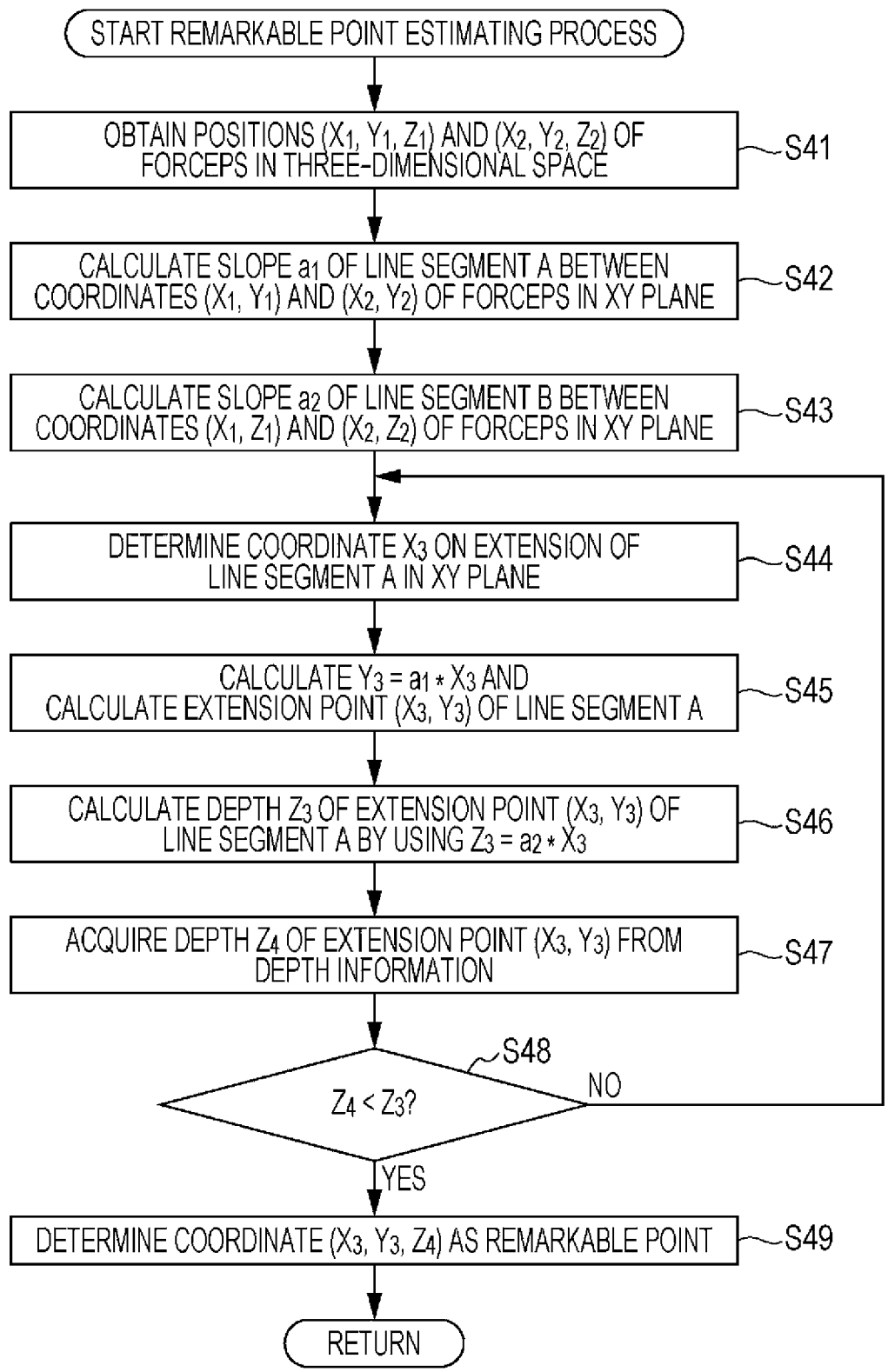
FIG. 10 is a flowchart illustrating a remarkable point estimating process in detail.

The remarkable point estimating process executed in Step S3 of FIG. 8 will be described in detail with reference to a flowchart of FIG. 10.

First, in Step S41, the remarkable point estimation section 43 obtains positions $(x_1, y_1, z_1)$ and $(x_2, y_2, z_2)$ of the forceps 81 in the surgery region image in the three-dimensional space which are supplied from the forceps position detection section 42.

In Step S42, the remarkable point estimation section 43 calculates a slope $a_1$ of a line segment A joining the coordinates $(x_i, y_i)$ and $(x_2, y_2)$ of the two points of the forceps in an XY plane. The slope $a_1$ may be calculated by using the following equation.

$$a_1=(Y_2-Y_1)/(X_2-X_1)$$

In Step S43, the remarkable point estimation section 43 calculates a slope $a_2$ of a line segment B joining the coordinates $(X_1, Z_1)$ and $(X_2, Z_2)$ of the two points of the forceps in an XZ plane. The slope $a_2$ may be calculated by using the following equation.

$$a_2=(Z_2-Z_1)/(X_2-X_1)$$

In Step S44, the remarkable point estimation section 43 determines a coordinate $X_3$ being an X coordinate value when the line segment A in the XY plane is extended by a predetermined length W in a center direction of the screen. The predetermined length W can be defined as 1/N (N is a positive integer) of the line segment A, for example.

In Step S45, the remarkable point estimation section 43 calculates $Y_3=a_1*X_3$ and calculates an extension point $(X_3, Y_3)$ of the line segment A in the XY plane. Here, "k" represents multiplication.

In Step S46, the remarkable point estimation section 43 calculates depth $Z_3$ of the extension point $(X_3,Y_3)$ of the line segment A in the XZ plane by using $Z_3=a_2*X_3$. Here, the calculated depth $Z_3$ of the extension point $(X_3, Y_3)$ of the line segment A in the XZ plane corresponds to a logical value of the extension point $(X_3, Y_3)$.

In Step S47, the remarkable point estimation section 43 acquires depth $Z_4$ of the extension point $(X_3, Y_3)$ of the line segment A from the depth information supplied from the depth information generation section 41. Here, the acquired depth $Z_4$ of the extension point $(X_3, Y_3)$ corresponds to a real value of the extension point $(X_3, Y_3)$.

In Step S48, the remarkable point estimation section 43 determines whether or not the depth $Z_3$ being the logical value of the extension point $(X_3, Y_3)$ is greater than the depth $Z_4$ being the real value of the extension point $(X_3, Y_3)$.

A case where the extension point $(X_3, Y_3)$ obtained by extending the line segment A which corresponds to the forceps 81 by the predetermined length W in the center direction of the screen is not included in the surgery region 82 means a case where the surgery region 82 is at a position deeper than the extension point $(X_3, Y_3)$. In this case, the depth $Z_4$ being the real value of the extension point $(X_3, Y_3)$ obtained from the depth information is greater than the depth $Z_3$ being the logical value.

On the other hand, when the surgery region 82 actually includes the extension point $(X_3, Y_3)$, the real value (depth $Z_4$) of the extension point $(X_3, Y_3)$ obtained from the depth information becomes ahead of the logical value (depth $Z_3$) of the extension point $(X_3, Y_3)$. Thus, the depth $Z_4$ being the real value of the extension point $(X_3, Y_3)$ is less than the depth $Z_3$ being the logical value.

Accordingly, in Step S48, the remarkable point estimation section 43 determines whether or not the logical value (depth $Z_3$) of the extension point $(X_3, Y_3)$ obtained by extending the line segment A by the predetermined length W becomes ahead of the real value (depth $Z_4$) of the extension point $(X_3, Y_3)$ obtained from the depth information.

In Step S48, when the depth $Z_3$ being the logical value of the extension point $(X_3, Y_3)$ is equal to or less than the depth $Z_4$ being the real value of the extension point $(X_3, Y_3)$, that is, when the depth $Z_3$ being the logical value of the extension point $(X_3, Y_3)$ is determined to be ahead of the depth $Z_4$ being the real value of the extension point $(X_3, Y_3)$, the process returns to Step S44.

In Step S44 to which the process returns, a coordinate $X_3$ obtained by extending the line segment A in the center direction of the screen to be deeper than the current extension point $(X_3, Y_3)$ by the predetermined length W in the XY plane is determined as a new coordinate $X_3$. Steps S45 to S48 which are described above are executed again on the determined new coordinate $X_3$.

On the other hand, in Step S48, when the depth $Z_3$ being the logical value of the extension point $(X_3, Y_3)$ is greater than the depth $Z_4$ being the real value, that is, when the depth $Z_4$ being the real value of the extension point $(X_3, Y_3)$ is determined to be ahead of the depth $Z_3$ being the logical value, the process proceeds to Step S49.

In Step S49, the remarkable point estimation section 43 determines an extension point $(X_3, Y_3, Z_4)$ which has the depth $Z_4$ being the real value as a Z coordinate value to be the remarkable point Q.

In this manner, Step S3 of FIG. 8 is completed and the process proceeds to Step S4.

In Step S4, the zoom image generation section 44 determines the area of interest QA in the surgery region image supplied from the imaging section 21. In Step S4, the area of interest QA which, for example, has the remarkable point Q as the center and has a size depending on the zoom magnification supplied from the operation control section 46 is determined.

Figure 11A:
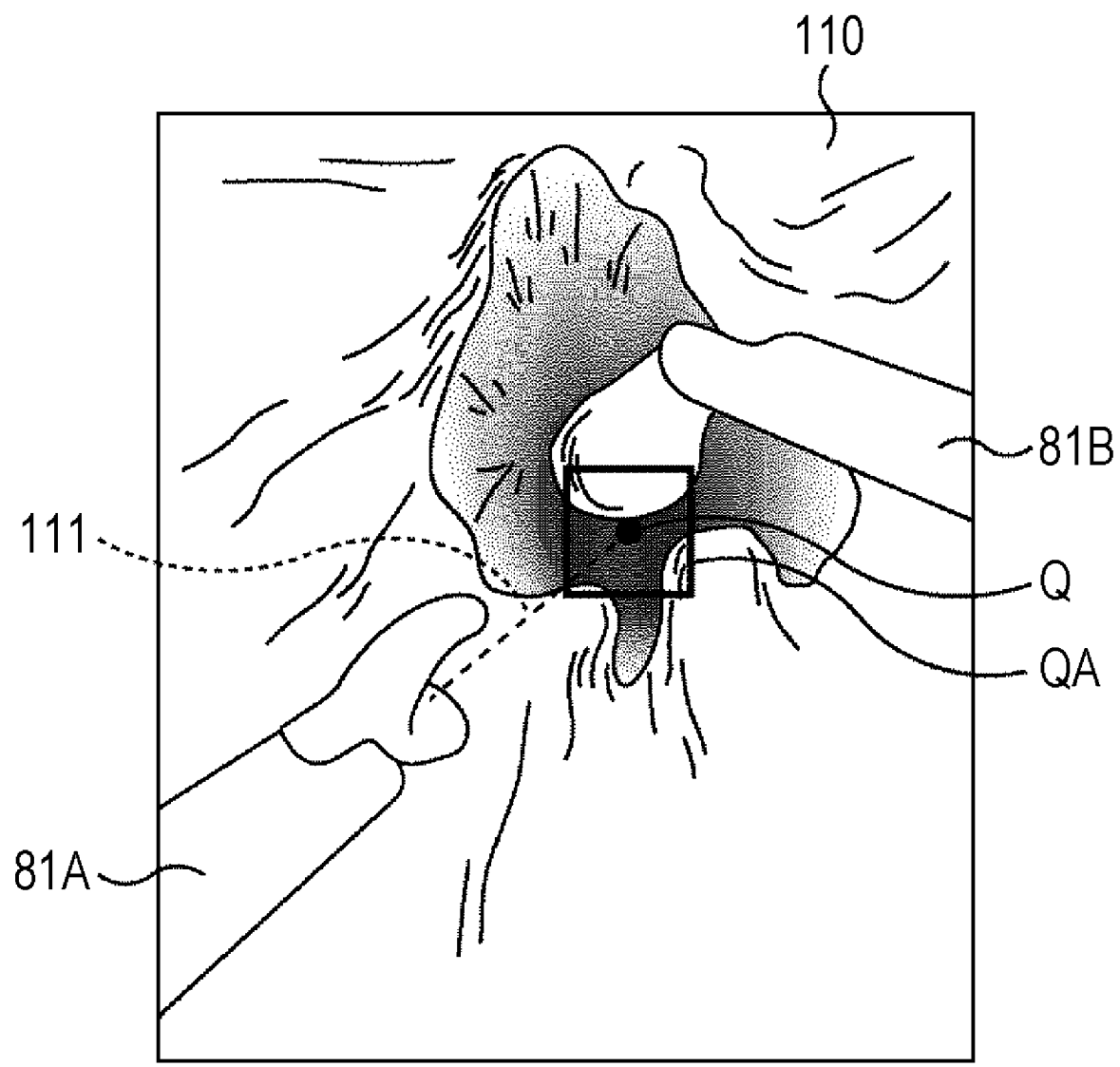
FIG. 11A is a diagram illustrating a different size of an area of interest depending on a zoom magnification.
Figure 11B:
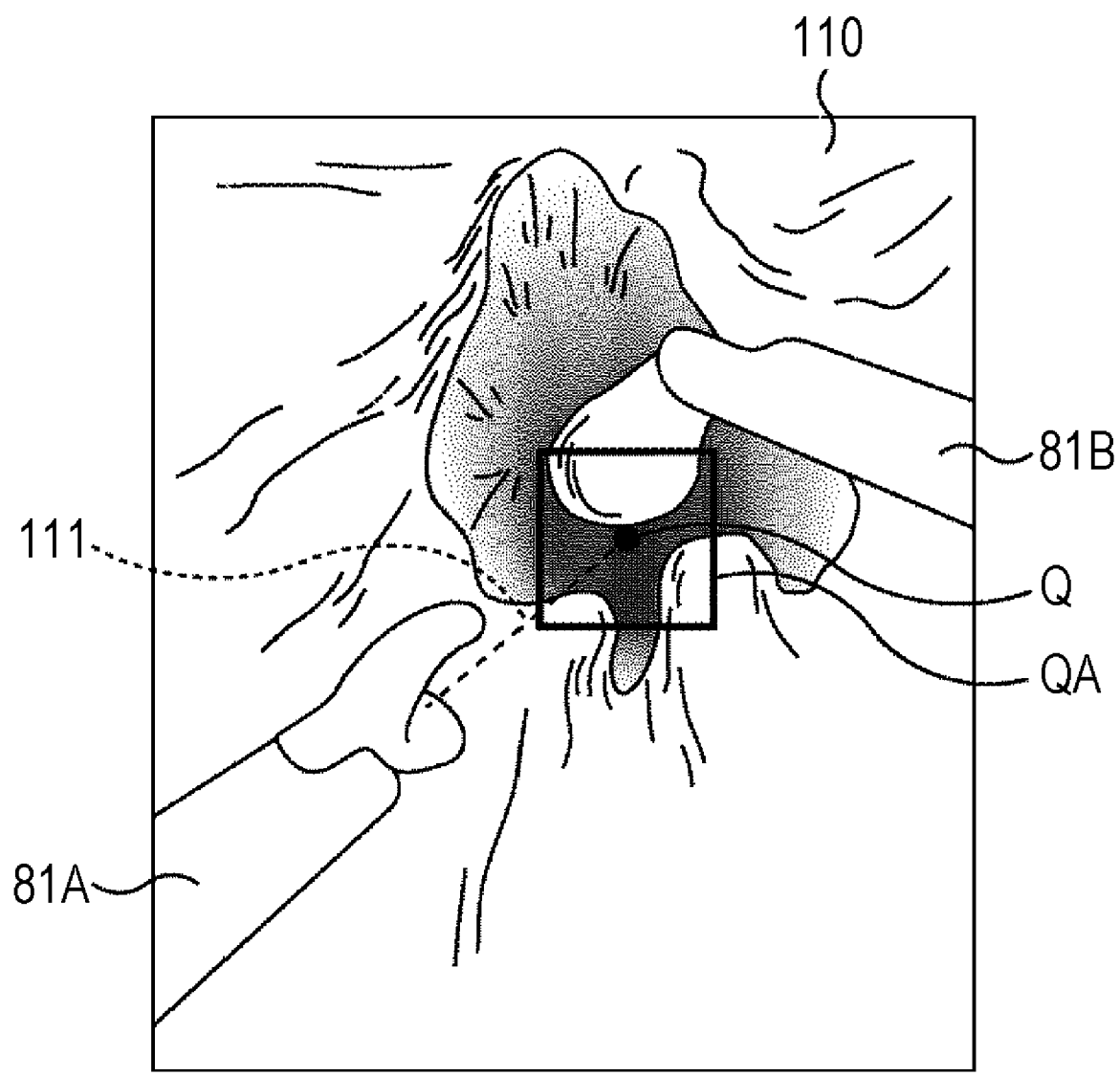
FIG. 11B is a diagram illustrating a different size of the area of interest depending on a zoom magnification.

FIG. 11A and FIG. 11B are diagrams illustrating the different sizes of the area of interest QA by the zoom magnification supplied from the operation control section 46.

FIG. 11A illustrates an example of the area of interest QA when the zoom magnification is high and FIG. 11B illustrates an example of the area of interest QA when the zoom magnification is low.

In this manner, as the zoom magnification of the surgery region image displayed on the display 14 becomes smaller, the area of interest QA which has a size becoming larger and has the remarkable point Q as the center may be set.

The size of the area of interest QA may be determined depending on a distance from the position (for example, $(x_2, y_2, z_2)$) of the recognized forceps 81 to the remarkable point Q, instead of the zoom magnification. In this case, as the distance from the forceps 81 to the remarkable point Q becomes longer, the area of interest QA which has the remarkable point Q as the center and has a size becoming wider is set.

If the process of Step S4 is completed, the process proceeds to Step S5. The zoom image generation section 44 generates the zoom image QB by expanding an image of the determined area of interest QA in accordance with the zoom magnification and supplies the generated zoom image to the image superposition section 45. The magnification for generating the zoom image QB (=(zoom image QB)/(image of area of interest QA)) may be determined in advance in accordance with the size of the area of interest QA. In addition, the magnification may be determined such that the size of the generated zoom image QB becomes equal to a predetermined size.

In Step S6, the image superposition section 45 executes a superposition position determining process of determining whether the zoom image QB supplied from the zoom image generation section 44 is superposed in the surgery region image supplied from the imaging section 21.

The superposition position determining process in Step S6 will be described with reference to FIG. 12A to FIG. 13.

Figure 12A:
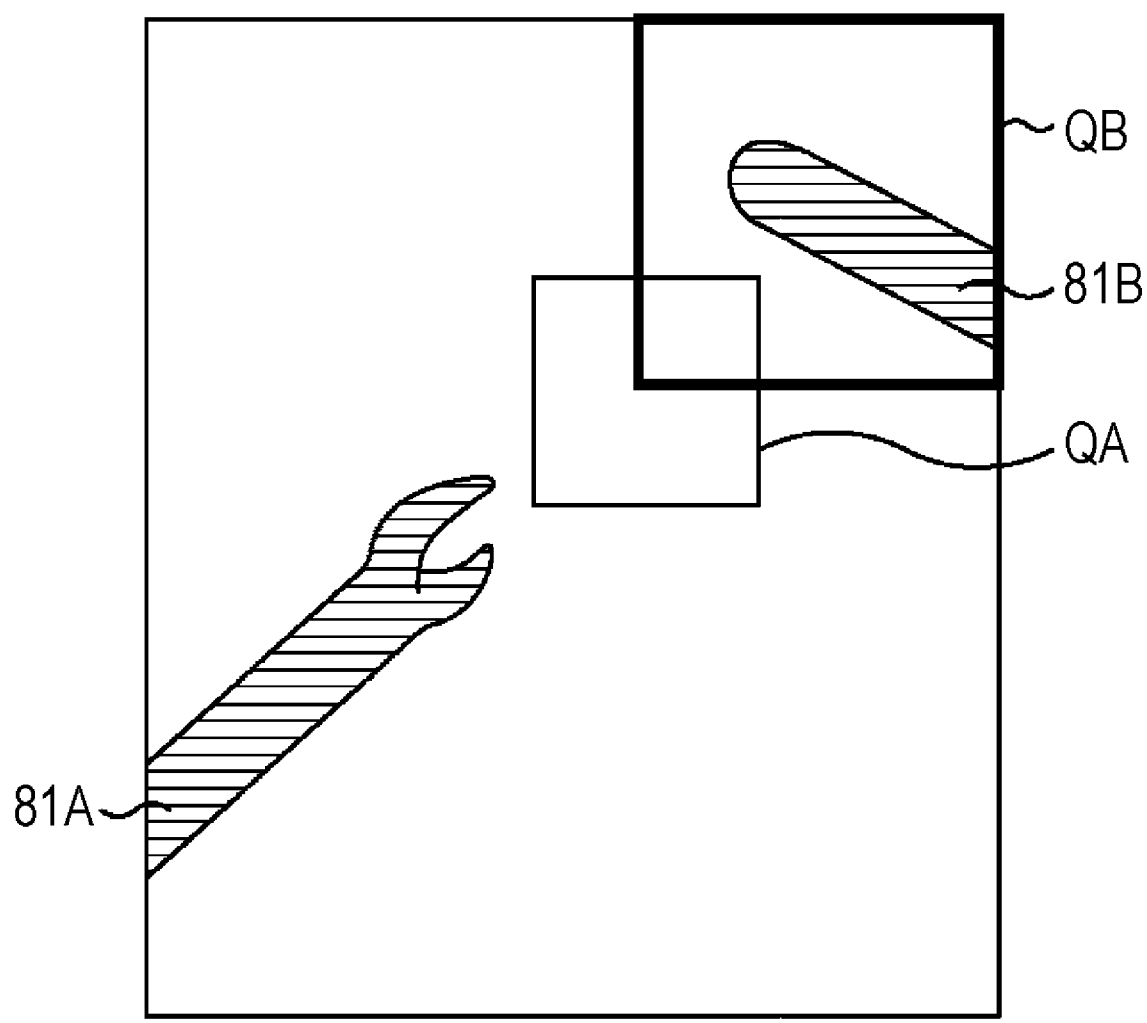
FIG. 12A is a diagram illustrating a superposition position determining process.

For example, as illustrated in FIG. 12A, if the superposed zoom image QB is overlapped with the area of interest QA or the important element such as the forceps 81, the area of interest QA or important element such as the forceps 81 is hidden by the zoom image QB, and thus performing surgery may be disturbed. For this reason, it is preferable that the zoom image QB is not disposed at a position at which the zoom image QB is overlapped with either of the area of interest QA and the important element such as the forceps 81.

Figure 12B:
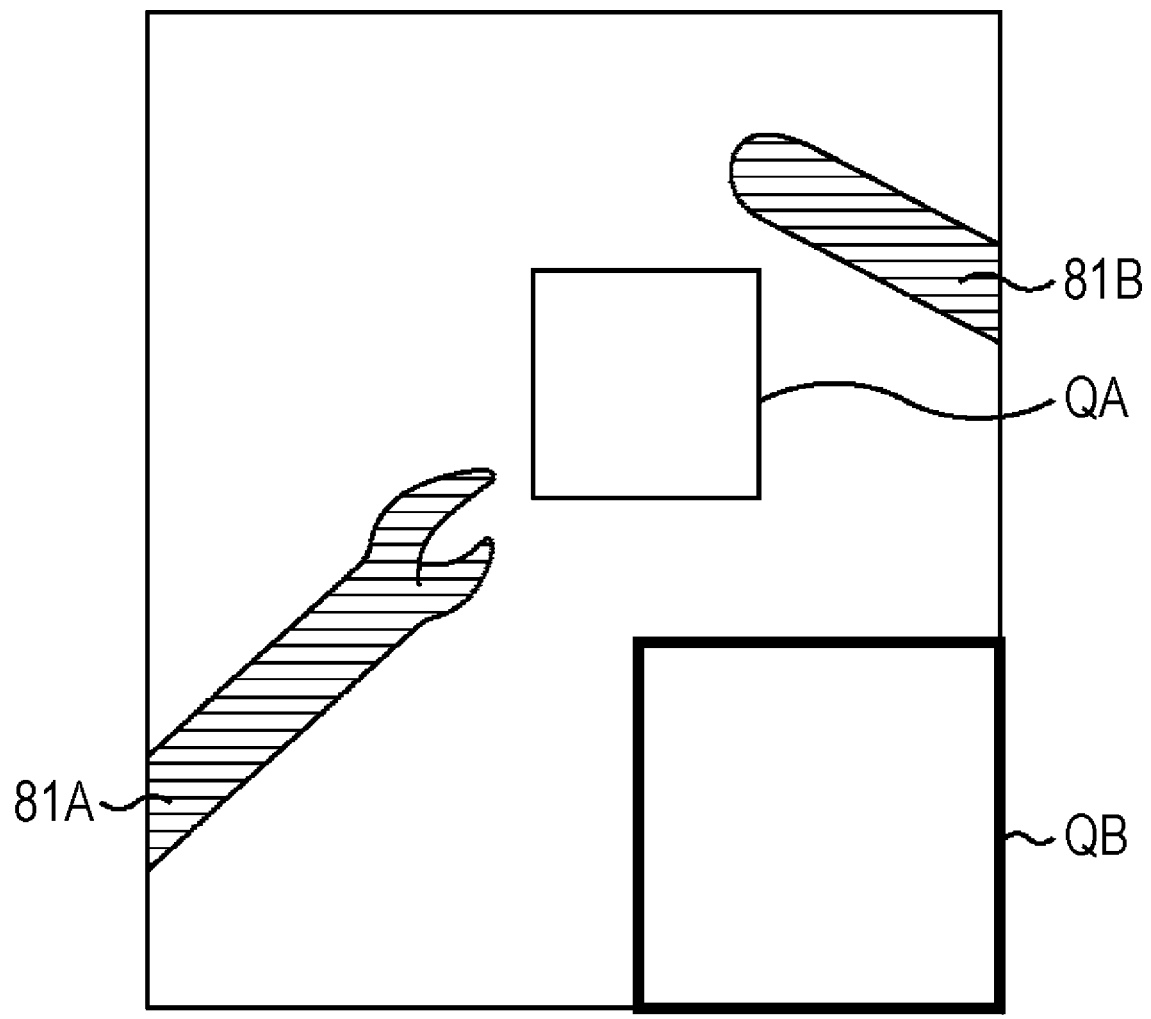
FIG. 12B is a diagram illustrating the superposition position determining process.

In other words, the zoom image QB is necessary to be disposed at which the zoom image QB is overlapped with neither of the area of interest QA and the important element such as the forceps 81, for example, as illustrated in FIG. 12B is only overlapped on the medical image and not the area of interest QA or the important element.

Accordingly, in the superposition position determining process of Step S6, when the zoom image QB is superposed, it is recognized that the zoom image QB is overlapped with neither of the area of interest QA and the important element such as the forceps 81, and then a superposition position of the zoom image QB is determined.

Figure 13:
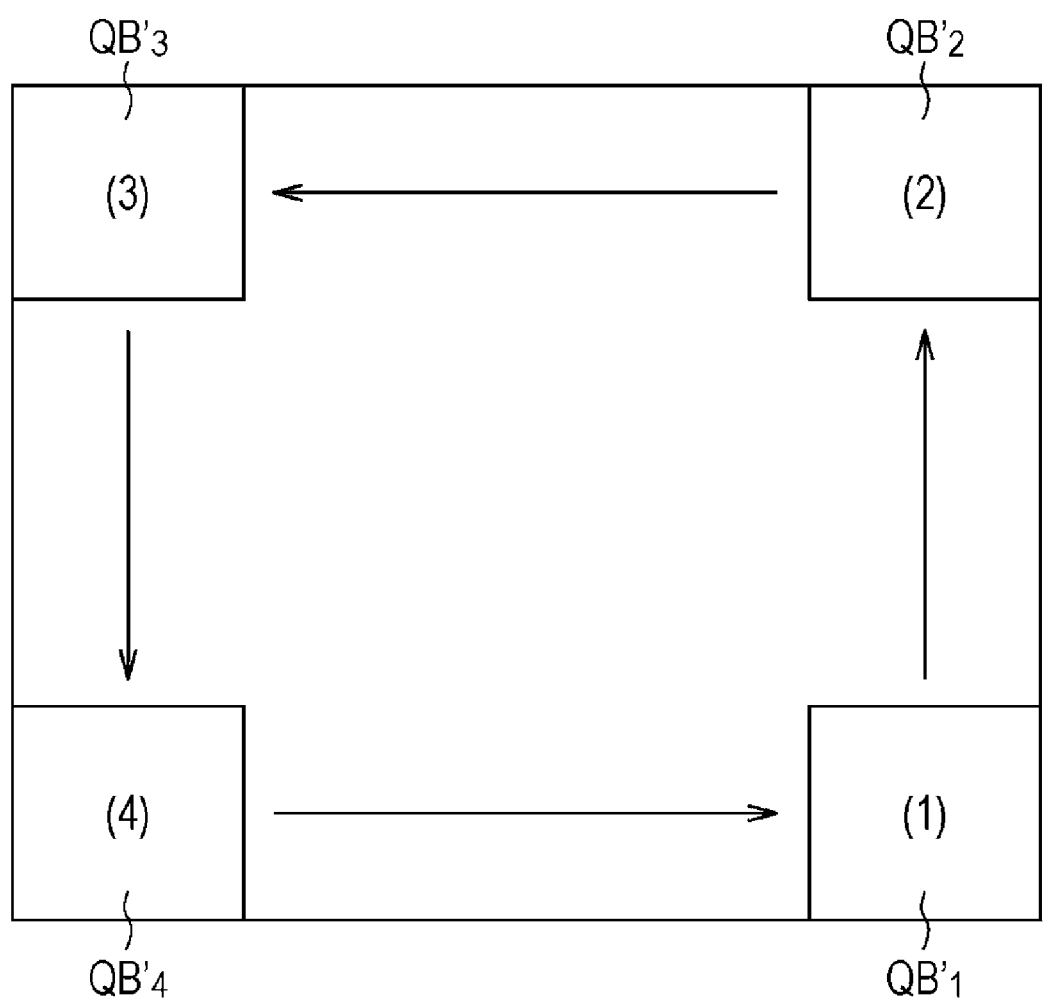
FIG. 13 is a diagram illustrating the superposition position determining process.

Specifically, the image superposition section 45 sets an area at the lower right corner in a display area of the display 14 as a candidate position $QB_1'$ of the superposition position, as illustrated in FIG. 13, and determines whether or not the candidate position $QB_1'$ is overlapped with either of the area of interest QA and the important element such as the forceps 81.

When the candidate position $QB_1'$ at the lower right corner is overlapped with either of the area of interest QA and the important element such as the forceps 81, the image superposition section 45 moves the candidate position QB' up and determines an area at the upper right corner in the display area of the display 14 to be the next candidate position $QB_2'$.

When the candidate position $QB_2'$ at the upper right corner is overlapped with either of the area of interest QA and the important element such as the forceps 81, the image superposition section 45 determines an area at the upper left corner in the display area of the display 14 to be the next candidate position $QB_3'$. When the candidate position $QB_3'$ at the upper right corner is also overlapped with either of the area of interest QA and the important element such as the forceps 81, an area at the lower left corner is determined to be the next candidate position $QB_4'$.

In the superposition position determining process, the superposition position of the zoom image QB is searched for in order not to interrupt the area of interest QA and the important element such as the forceps 81, as described above. When there is no superposition position at which the area of interest QA and the important element such as the forceps 81 are not interrupted, the image superposition section 45 does not perform superposition.

A searching order of the candidate positions $QB_1'$ to $QB_4'$ is not limited to the above-described example. The zoom image QB may be disposed at a position other than the four corners of the surgery region image if there is a position at which the area of interest QA and the important element such as the forceps 81 are not interrupted.

<Detailed Flow of Superposition Position Determining Process>

The superposition position determining process executed in Step S6 of FIG. 8 will be described with reference to flowcharts of FIG. 14A and FIG. 14B.

First, in Step S61, the image superposition section 45 obtains the size of the zoom image QB supplied from the zoom image generation section 44.

In Step S62, the image superposition section 45 determines the candidate position QB' of the superposition position for superposing the zoom image QB. In this embodiment, as described above, the area at the lower right corner in the display area of the display 14 is determined to be a first candidate position $QB_1'$.

In Step S63, the image superposition section 45 determines whether the determined candidate position $QB_1'$ at the lower right corner is not overlapped with the area of interest QA and the important element such as the forceps 81 in the surgery region image imaged by the imaging section 21. The position of the important element such as the forceps 81 in the surgery region image may be recognized by using position information of the important element such as the forceps detected through the forceps/area position detecting process of Step S2 and may be recognized by using other methods. For example, the forceps 81 is made of metal in general and it is easy to distinguish a color (red) in the body between silver-based colors (color of metal). Thus, the forceps 81 may be detected by recognizing the color and the like. The forceps position detection process may detect the position from one or more of color difference information, brightness, and depth independent from or in concert with edge detection techniques. The area position detecting process may detect the important area as is noted above.

In Step S63, when the determined candidate position $QB_1'$ at the lower right corner is determined not to be overlapped with the area of interest QA or the forceps 81, the process proceeds to Step S71.

On the other hand, in Step S63, when the determined candidate position $QB_1'$ at the lower right corner is determined to be overlapped with the area of interest QA or the important object such as the forceps 81, the process proceeds to Step S64. The image superposition section 45 moves the candidate position QB' up and determines the area at the upper right corner in the display area of the display 14 to be as the candidate position $QB_2'$.

In Step S65, the image superposition section 45 determines whether the determined candidate position $QB_2'$ at the upper right corner is not overlapped with the area of interest QA or the important object such as the forceps 81 in the surgery region image imaged by the imaging section 21.

In Step S65, when the determined candidate position $QB_2'$ at the upper right corner is determined not to be overlapped with the area of interest QA or the important object such as the forceps 81, the process proceeds to Step S71.

On the other hand, in Step S65, when the determined candidate position $QB_2'$ at the lower right corner is determined to be overlapped with the area of interest QA or the important object such as the forceps 81, the process proceeds to Step S66. The image superposition section 45 moves the candidate position QB' left and determines the area at the upper left corner in the display area of the display 14 to be as the candidate position $QB_3'$.

In Step S67, the image superposition section 45 determines whether the determined candidate position $QB_3'$ at the upper left corner is not overlapped with the area of interest QA or the important object such as the forceps 81 in the surgery region image imaged by the imaging section 21.

In Step S67, when the determined candidate position $QB_3'$ at the upper left corner is determined not to be overlapped with the area of interest QA or the important object such as the forceps 81, the process proceeds to Step S71.

On the other hand, in Step S67, when the determined candidate position $QB_3'$ at the upper left corner is determined to be overlapped with the area of interest QA or the important object such as the forceps 81, the process proceeds to Step S68. The image superposition section 45 moves the candidate position QB' down and determines the area at the lower left corner in the display area of the display 14 to be as the candidate position $QB_4'$.

In Step S69, the image superposition section 45 determines whether the determined candidate position $QB_4'$ at the lower left corner is not overlapped with the area of interest QA or the important object such as the forceps 81 in the surgery region image imaged by the imaging section 21.

In Step S69, when the determined candidate position $QB_4'$ at the lower left corner is determined not to be overlapped with the area of interest QA or the important object such as the forceps 81, the process proceeds to Step S71.

On the other hand, in Step S69, when the determined candidate position $QB_4'$ at the lower left corner is determined to be overlapped with the area of interest QA or the important object such as the forceps 81, the process proceeds to Step S70 and the image superposition section 45 determines not to perform superposition.

In Step S71, the image superposition section 45 determines the determined candidate position QB' (either of the candidate positions $QB_1'$ to $QB_4'$) at which the determined candidate position QB' is not overlapped with the area of interest QA or the important object such as the forceps 81 in Step S63, S65, S67, or S69 which is described above to be the superposition position of the zoom image QB.

As described above, in the superposition position determining process of the Step S6 in FIG. 8, the position at which the area of interest QA and the important object such as the forceps 81 are not interrupted is determined to be the superposition position of the zoom image QB.

The superposition position determining process of Step S6 is completed and then the process proceeds to Step S7. The image superposition section 45 confirms that the superposition position is determined through the superposition position determining process.

In Step S7, when it is confirmed that the superposition position is determined, the process proceeds to Step S8. The image superposition section 45 superposes the zoom image QB on the surgery region image supplied from the imaging section 21 at the determined superposition position and displays an image obtained through superposition on the display 14.

Figure 14A:
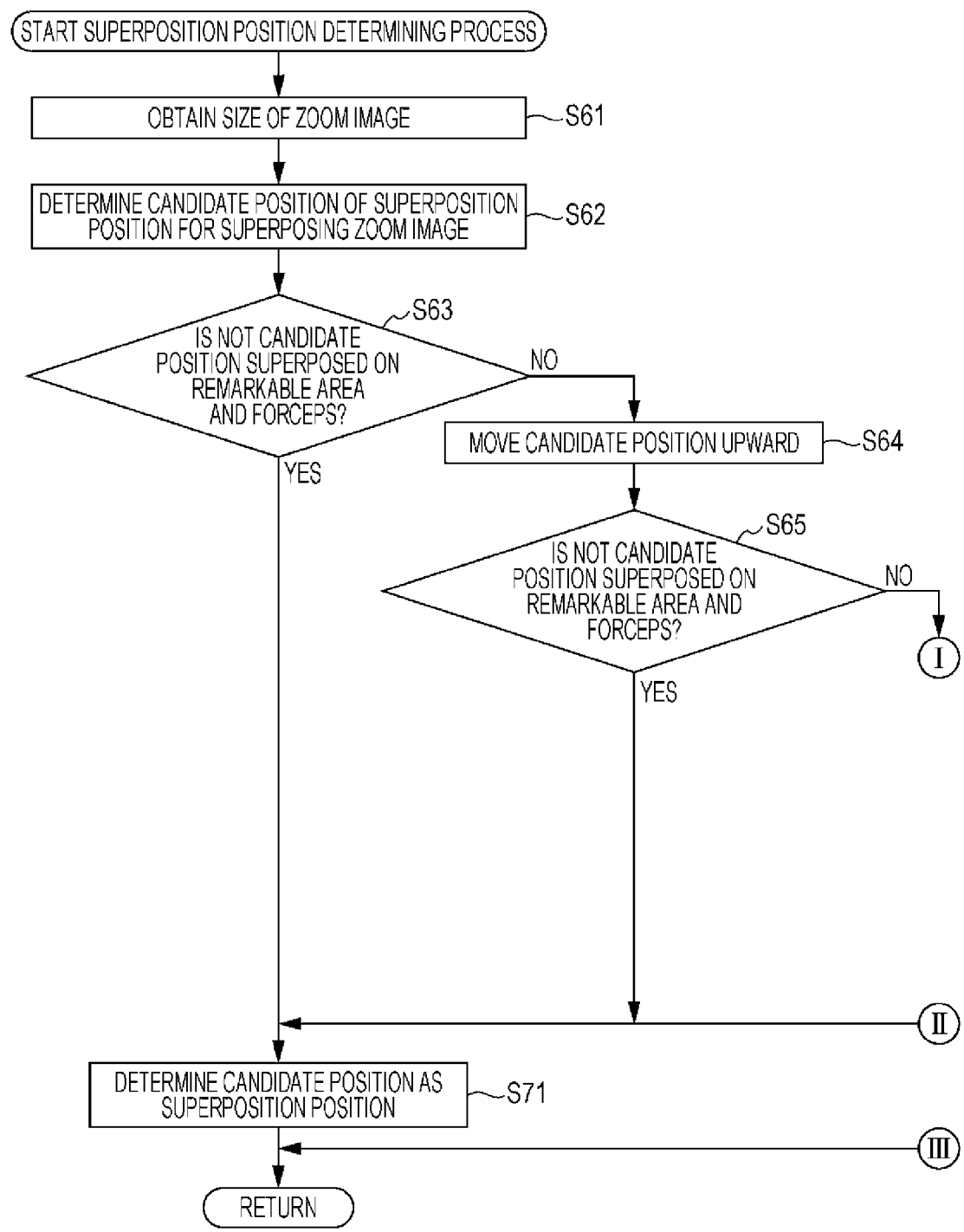
FIG. 14A is a flowchart illustrating the superposition position determining process in detail.
Figure 14B:
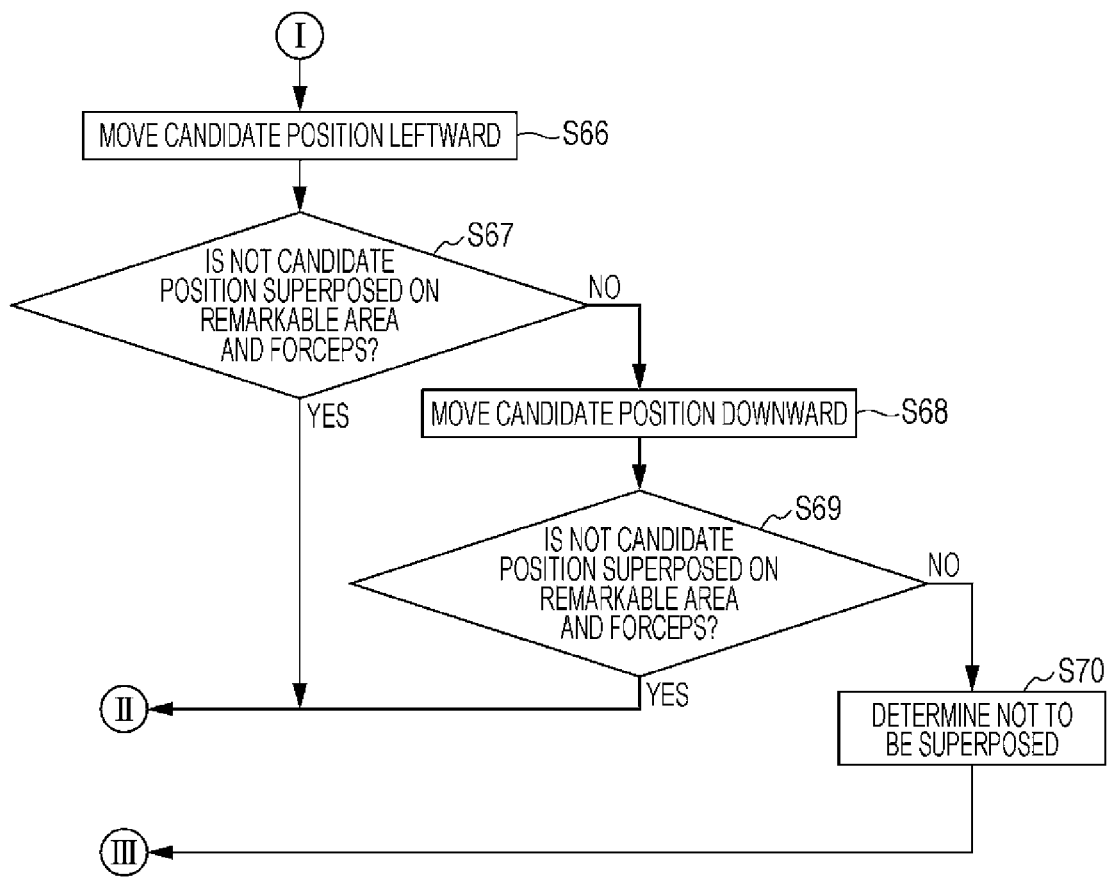
FIG. 14B is a flowchart illustrating the superposition position determining process in detail.

On the other hand, in Step S7, when it is confirmed that the superposition position is not determined, that is, when it is determined that superposition is not performed in the superposition position determining process of FIG. 14A and FIG. 14B, the process proceeds to Step S9. The image superposition section 45 does not superpose the zoom image QB, but displays only the surgery region image supplied from the imaging section 21 on the display 14.

Accordingly, the superposition displaying process is completed.

The superposition displaying process of FIG. 8 may be repeated during a time period when the superposition mode is set to be ON.

In the superposition displaying process of FIG. 8, the forceps/area position detecting process and the remarkable point estimating process are executed each time the surgery region image is supplied from the imaging sensor 24. However, the forceps/area position detecting process and the remarkable point estimating process may be executed for each predetermined period, for example, once for tens of frames, instead of being executed for each frame.

When the superposition displaying process of FIG. 8 is repeated, the superposition position of the zoom image QB may be changed depending on a change of the position of the important object such as the forceps 81, and the like. When the superposition position of the zoom image QB is changed, the superposition position at that time does not move instantly to the next superposition position, but may move slowly at a speed allowed to visually recognize the zoom image QB. In this manner, the zoom image QB may be recognized easily by the practitioner.

The zoom image QB is obtained not only by expanding an image of the area of interest QA with predetermined magnification. The zoom image QB may be obtained by executing, for example, a predetermined color conversion process such as a gamma correction process, an enhancement process of a specified color matched with the color of the area of interest QA for easily recognizing a region of performing surgery, or a contrast adjustment process. A predetermined color conversion process may be executed on the entirety of the surgery region image in addition to the zoom image QB.

According to the above-described superposition displaying process, the important object such as the forceps 81 is detected from the surgery region image obtained by the imaging section 21 performing imaging and the remarkable point Q on which the practitioner focuses is estimated from the detected important object such as forceps 81. The area of interest QA is determined based on the remarkable point Q and the zoom image QB obtained by expanding an image of the area of interest QA with predetermined magnification is disposed and superposed at a position at which the area of interest QA and the forceps 814 are not interrupted in the surgery region image.

Accordingly, since the zoom image QB obtained by expanding the area of interest QA for performing surgery is displayed on the display 14 (automatically by the CCU 12) though the practitioner does not perform a special operation, it is not necessary that the practitioner stops performing surgery. That is, according to the superposition displaying process, it is possible to display the surgery region desired by the practitioner without an effort of the practitioner.

In addition, a function of superposing the zoom image QB which is obtained by expanding the area of interest QA may be unnecessary in some cases. In those cases, since ON and OFF of the superposition mode may be switched by using the foot pedal 61, the practitioner can use a superposition function (superposition mode) only in a necessary case without stopping performing of surgery.

In the endoscope system of FIG. 1, the high resolution imaging sensor such as a 4K camera may be used as the imaging sensor 24 and thus it is possible to display the zoom image QB obtained by expanding the area of interest QA with high image quality.

In the above-described forceps position detecting process, the example is described in which the forceps 81 is detected by generating a parallax image from the depth information of the surgery region image and detecting a linear edge. However, other detecting methods may be employed.

For example, marks may be marked on two predetermined locations of the forceps 81 and the two marks marked on the forceps 81 may be detected as positions $(x_1,y_1,z_1)$ and $(x_2,y_2,z_2)$ of the forceps 81 in the surgery region image. Characteristics such as a shape and a color of the forceps 81, and a shape and a color of the mark marked on the forceps 81 of various forceps 81 used in performing surgery are stored in advance in a memory of the forceps position detection section 42 as a database and the mark may be detected based on information on the designated forceps 81.

<Process Flow of 2D/3D Display Switching Process>

The surgery region is imaged by the two imaging sensors 24 in the endoscope system of FIG. 1. Thus, both of the 3D display using an R image and an L image and the 2D display using either of the R image and the L image may be applied. The practitioner may switch the 3D display and the 2D display as necessary and cause display to be performed on the display 14 in the switched display manner.

Figure 15:
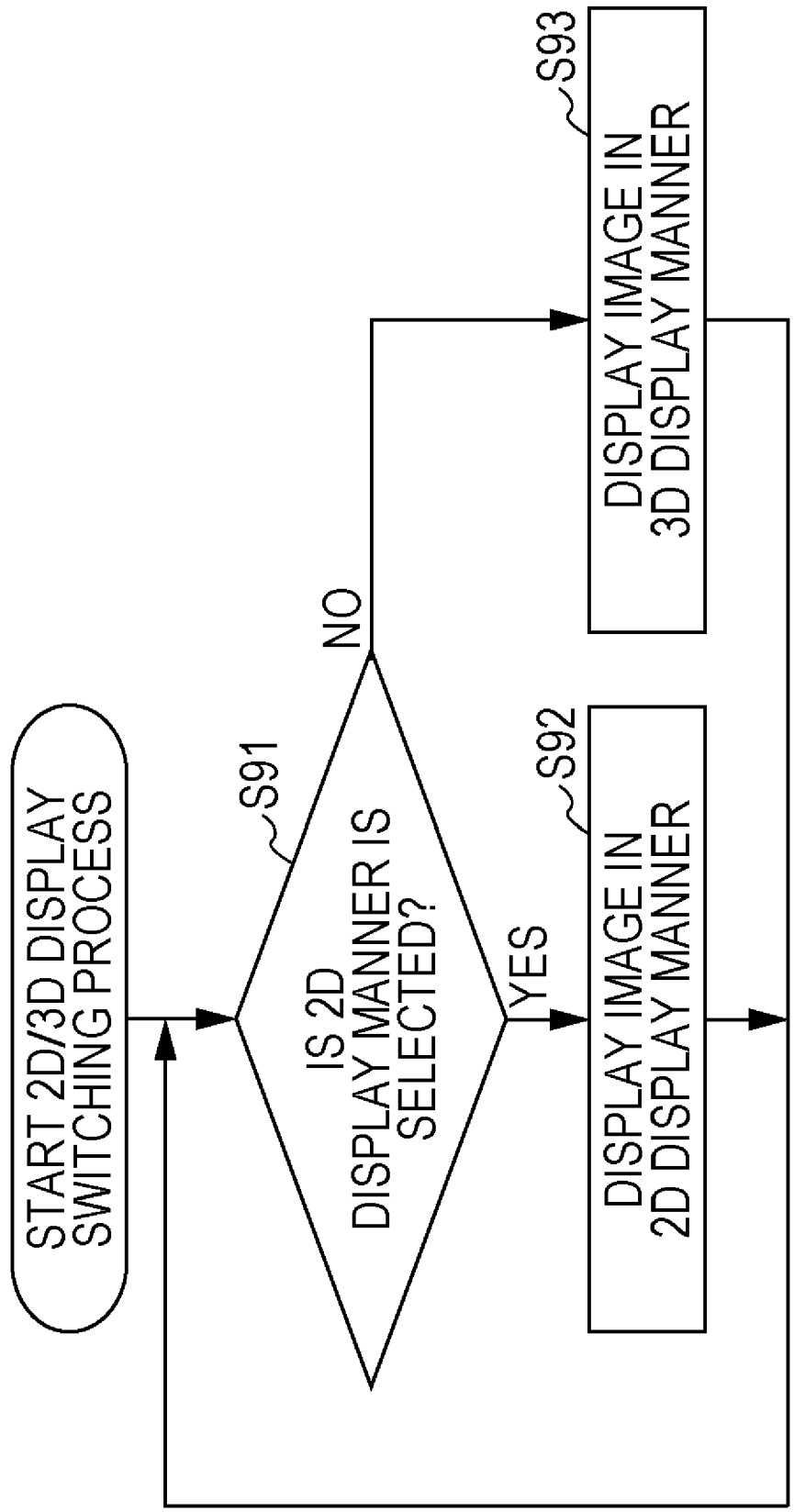
FIG. 15 is a flowchart illustrating a 2D/3D display switching process.

FIG. 15 illustrates a flowchart of a 2D/3D display switching process in which the 3D display and the 2D display are switched and display is performed in the switched display manner. This process may be started with supplying power to the CCU 12, for example.

First, in Step S91, the operation control section 46 determines whether or not the 2D display is selected, based on an operation signal supplied from the operation section 13. The practitioner may switch the 2D display and the 3D display by using the foot pedal 61, for example.

In Step S91, when it is determined that the 2D display is selected, the process proceeds to Step S92. The operation control section 46 supplies display mode information indicating that display is performed in the 2D display manner to the image superposition section 45. The image superposition section 45 which obtains the display mode information supplies only one of an R image and an L image supplied from the imaging section 21 to the display 14 and displays the surgery region image in the 2D display manner.

On the other hand, when it is determined that the 3D display is selected in Step S91, the process proceeds to Step S93. The operation control section 46 supplies display mode information indicating that display is performed in the 3D display manner to the image superposition section 45. The image superposition section 45 which obtains the display mode information alternately supplies the R image and the L image which are supplied from the imaging section 21 to the display 14 and displays the surgery region image in the 3D display manner.

After Step S92 or S93, the process returns to Step S91 again and the subsequent processes are repeated. With this, the 2D display or the 3D display is performed in the display 14 in accordance with designation of the practitioner until the power of the CCU 12 turns OFF.

The practitioner can select desired one of the 3D display and the 2D display and cause the surgery region image to be displayed on the display 14 through the above-described 2D/3D display switching process.

The present disclosure may be similarly applied to a microscope system in addition to the above-described endoscope system. In this case, a microscope camera head is provided instead of the endoscope camera head 11 in FIG. 1 and the CCU 12 may execute the superposition displaying process of a surgery region image imaged by the microscope camera head.

An image process executed by the CCU 12 may be executed with hardware or software. When a series of processes are executed with software, a program constituting the software is installed on a computer. Here, the computer includes a computer obtained by combining dedicated hardware, a general personal computer allowed to perform various functions by installing various programs, and the like.

Figure 16:
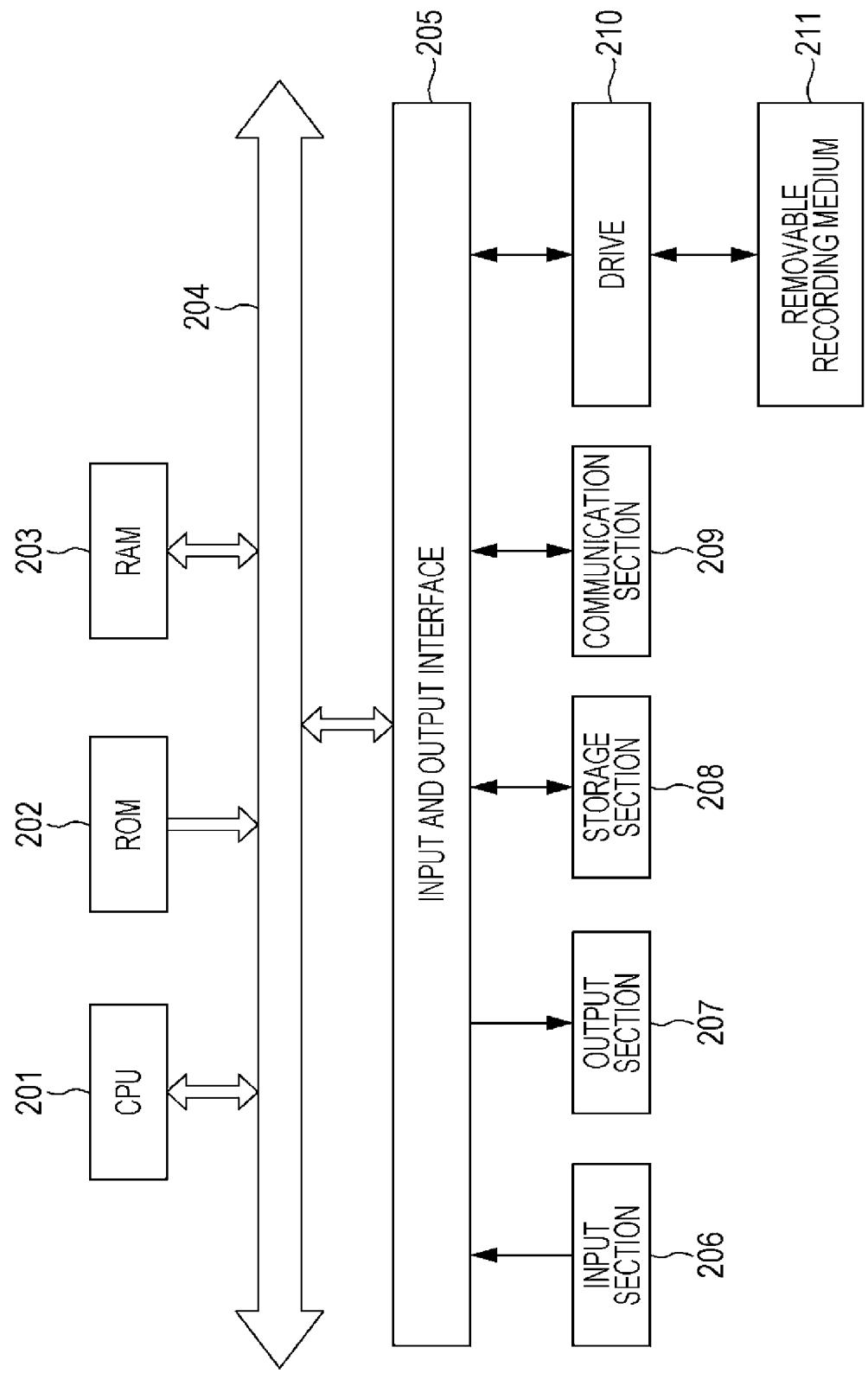
FIG. 16 is a block diagram illustrating a configuration example of an embodiment of a computer according to the present disclosure.

FIG. 16 is a block diagram illustrating a configuration example of hardware of a computer in which the CCU 12 executes an image process by using a program.

In the computer, a central processing unit (CPU) 201, a read only memory (ROM) 202, and a random access memory (RAM) 203 are connected to each other through a bus 204.

An input and output interface 205 is connected to the bus 204. An input section 206, an output section 207, a storage section 208, a communication section 209, and a drive 210 are connected to the input and output interface 205.

The input section 206 is configured by a keyboard, a mouse, a microphone, and the like. The output section 207 is configured by a display, a speaker, and the like. The storage section 208 is configured by a hard disk, a non-volatile memory, and the like. The communication section 209 is configured by a network interface and the like. The drive 210 drives a removable recording medium 211 such as a magnetic disk, an optical disc, a magneto-optical disk, and a semiconductor.

In the computer configured as described above, the CPU 201 executes the above-described series of processes by loading a program stored in the storage section 208 on the RAM 203 through the input and output interface 205 and the bus 204 and executing the loaded program, for example.

In the computer, the program may be installed on the storage section 208 through the input and output interface 205 by mounting the removable recording medium 211 on the drive 210. The program may be received in the communication section 209 through a wired or wireless transmission medium such as a local area network, the Internet, and satellite data broadcasting and may be installed on the storage section 208. In addition, the program may be installed on the ROM 202 or the storage section 208 in advance.

In this specification, the steps illustrated in the flowcharts may be executed in time series in the illustrated order. The steps may be executed not necessarily in time series, but in parallel or at a necessary timing, for example, when calling is performed, and the like.

In this specification, the system means a set of multiple constituents (apparatus, module (component), and the like) and it is not necessary that all of the constituents are in the same housing. Accordingly, the system includes a plurality of apparatuses which are stored in separate housings and connected to each other through a network and one apparatus in which a plurality of modules are stored in one housing.

The present disclosure refers to a process relating to superposition display of an image obtained by the imaging section 21 of the endoscope system and an expanded image of a portion of the image. However, the present disclosure may be applied to superposition display of a general captured image other than a medical system such as the endoscope system. That is, the present disclosure may be applied to a case in which a remarkable point on which an operator focuses, and an area of interest are determined based on a three-dimensional position of instructing tool, an operating mechanism, an apparatus, or the like (corresponding to the above-described surgical instrument) shown in a captured image, and an image obtained by expanding an image of the area of interest is superposed on the captured image and displayed on a screen.

The embodiment of the present disclosure is not limited to the above-described embodiment and may be changed variously without departing the gist of the present disclosure.

For example, an embodiment obtained by combining some or all of the above-described embodiments may be employed.

For example, the present disclosure may have a configuration of cloud computing in which one function is distributed by a plurality of apparatuses through a network and the plurality of apparatuses together process the function.

Each step illustrated in the above-described flowcharts may be executed in one apparatus or may be distributed and executed in a plurality of apparatuses.

Furthermore, when one step includes a plurality of processes, the plurality of processes included in the one step may be executed in one apparatus or may be distributed and executed in a plurality of apparatuses.

The effects described in this specification are only examples and are not limited thereto. There may be effects other than the effects described in this specification.

The present disclosure may have the following configurations.

(1)

A medical imaging apparatus, comprising:
a controller including circuitry configured to
control display on a display area of a medical image,
control display on the display area of a superimposed image corresponding to the medical image such that the superimposed image is displayed overlapped on the medical image,
detect a position of an important element within the medical image, and
determine a position of the superimposed image within the display area, based on the detected position of the important element, such that the superimposed image does not overlap on the important element within the medical image.

(2)

The medical imaging apparatus according to (1), wherein the controller including circuitry is further configured to detect an overlap between a portion of the important element and the portion of the superimposed image within the display area and adjust, in response to the overlap being detected, the position of the superimposed image within the display area such that superimposed image is no longer overlapping on the portion of the important element within the medical image.

(3)

The medical imaging apparatus according to (1)-(2), wherein the medical image includes a surgical image of a body.

(4)

The medical imaging apparatus according to (1)-(3), wherein the important element is an important object or an important area.

(5)

The medical imaging apparatus according to (1)-(4), wherein the superimposed image corresponds to a region of interest portion of the medical image.

(6)

The medical imaging apparatus according to (1)-(5), wherein the superimposed image is a zoomed image corresponding to a region of interest portion of the medical image.

(7)

The medical imaging apparatus according to (1)-(6), wherein the superimposed image corresponds to a region of interest portion of the medical image and the region of interest is estimated from a three-dimensional posture of the important element.

(8)

The medical imaging apparatus according to claim (1)-(7), wherein the important element is a surgical instrument.

(9)

The medical imaging apparatus according to (1)-(8), wherein the controller including the circuitry is further configured to
detect a second position of the important element within the medical image after movement of the important element within the medical image,
detect a second overlap between the detected second position of the important element and the adjusted position of the superimposed image, and
further adjust, in response to the second overlap being detected, the adjusted position of the superimposed image within the display area such that the superimposed image is no longer overlapping on the detected second position of the important element within the medical image.

(10)

The medical imaging apparatus according to (5), wherein the circuitry is configured to control display on the display area of a frame indicating the region of interest portion.

(11)

The medical imaging apparatus according to (1)-(10), wherein the superimposed image is positioned in any one of four corners of the medical image.

(12)

The medical imaging apparatus according to (1)-(11), wherein the superimposed image is subjected to a color conversion process.

(13)

A method for processing a medical image by a medical imaging apparatus including a controller including circuitry, the method comprising:
controlling display on a display area of a medical image,
controlling display on the display area of a superimposed image corresponding to the medical image such that the superimposed image is displayed overlapped on the medical image,
detecting, by the circuitry, a position of an important element within the medical image, and
determining a position of the superimposed image within the display area, based on the detected position of the important element, such that the superimposed image does not overlap on the important element within the medical image.

(14)

A non-transitory computer readable medium having stored thereon a program that
when executed by a computer causes the computer to implement a method for processing a medical image by a medical imaging apparatus including a controller including circuitry, the method comprising:
controlling display on a display area of a medical image,
controlling display on the display area of a superimposed image corresponding to the medical image such that the superimposed image is displayed overlapped on the medical image,
detecting, by the circuitry, a position of an important element within the medical image, and
determining a position of the superimposed image within the display area, based on the detected position of the important element, such that the superimposed image does not overlap on the important element within the medical image.

(15)

A medical imaging system, comprising:
a medical imaging device that obtains a medical image;
a display device having a display area;
a controller including circuitry configured to
control display on the display area of the display device of the medical image obtained by the medical imaging device,
control display on the display area of the display device of a superimposed image corresponding to the medical image such that the superimposed image is displayed overlapped on the medical image,
detect a position of an important element within the medical image, and determine a position of the superimposed image within the display area, based on the detected position of the important element, such that the superimposed image does not overlap on the important element within the medical image.

(16)

The system according to (15), wherein the medical imaging device is an endoscope or a surgical microscope.

(A1)

An image processing apparatus including: a zoom image generation section configured to generate a zoom image from an image obtained by imaging a surgical field which includes a region of a surgical target by expanding an image of an area of interest on which a practitioner focuses; and an image superposition section configured to superpose the zoom image on the image and display an image through superposition on a screen.

(A2)

The apparatus according to (A1), in which the area of interest is determined based on a three-dimensional position of a surgical instrument in the image.

(A3)

The apparatus according to (A2), in which the area of interest is determined to include a tip end portion of the surgical instrument.

(A4)

The apparatus according to (A2), in which the area of interest is determined to include an intersection point of the region and an extension line obtained by extending a line segment corresponding to the three-dimensional position of the surgical instrument.

(A5)

The apparatus according to (A2), in which the area of interest is determined to include a tip end portion of the surgical instrument and an intersection point of the region and an extension line obtained by extending a line segment corresponding to the three-dimensional position of the surgical instrument.

(A6)

The apparatus according to any one of (A3) to (A5), in which zoom magnification when the image is obtained is set such that the tip end portion of the surgical instrument and the intersection point of the region and the extension line obtained by extending the line segment corresponding to the three-dimensional position of the surgical instrument are included.

(A7)

The apparatus according to (A2), in which the three-dimensional position of the surgical instrument is detected based on information on a linear edge in the image.

(A8)

The apparatus according to (A7), in which the information on the linear edge in the image is detected based on brightness information of the image.

(A9)

The apparatus according to (A7), in which the information on the linear edge in the image is detected based on color information of the image.

(A10)

The apparatus according to any one of (A2) to (A6), in which the three-dimensional position of the surgical instrument is detected by detecting a marker attached to the surgical instrument in the image.

(A11)

The apparatus according to any one of (A2) to (A10), in which the image superposition section displays the area of interest on which the practitioner focuses and is determined based on the three-dimensional position of the surgical instrument, on the screen.

(A12)

The apparatus according to (A11), in which the image superposition section displays an extension line obtained by extending a line segment corresponding to the three-dimensional position of the surgical instrument from the surgical instrument to the remarkable point, on the screen.

(A13)

The apparatus according to any one of (A1) to (A12), in which the image superposition section displays a frame for indicating the area of interest on the screen.

(A14)

The apparatus according to any one of (A1) to (A13), in which the image superposition section disposes the zoom image on any one of four corners of the image.

(A15)

The apparatus according to any one of (A1) to (A14), in which the image superposition section disposes the zoom image at a position at which the zoom image is overlapped with neither of the surgical instrument and the area of interest in the image.

(A16)

The apparatus according to any one of (A1) to (A15), in which the zoom image generation section generates a zoom image obtained by expanding an image of the area of interest with magnification determined depending on a distance from the surgical instrument in the image to the remarkable point at the area of interest.

(A17)

The apparatus according to any one of (A1) to (A16), in which the image superposition section performs a predetermined color conversion process on the image or the zoom image and superposes either the image or the zoom image subjected to the color conversion process on the other.

(A18)

The apparatus according to any one of (A1) to (A17), in which the image superposition section superposes the zoom image on the image when a superposition mode is ON.

(A19)

An image processing method for causing the image processing apparatus to generate a zoom image from an image obtained by imaging a surgical field which includes a region of a surgical target by expanding an image of an area of interest on which a practitioner focuses and to superpose the zoom image on the image to display an image through superposition on a screen.

(B1)
An image processing apparatus including: a position detection section configured to obtain depth information of a plurality of images calculated from the images which are obtained by a plurality of imaging sections imaging a surgery region being a region of a surgical target and to detect a three-dimensional position of a surgical instrument in the image by using the obtained depth information of the images.

(B2)
The apparatus according to (B1) further including: a remarkable point estimation section configured to estimate a remarkable point of a practitioner who operates the surgical instrument, based on the detected three-dimensional position of the surgical instrument.

(B3)
The apparatus according to (B2), in which the remarkable point estimation section estimates an intersection point of the surgery region and an extension line obtained by extending a line segment corresponding to the three-dimensional position of the surgical instrument, as the remarkable point.

(B4)
The apparatus according to (B2) or (B3) further including: a zoom image generation section configured to determine an area of interest on which the practitioner focuses based on the estimated remarkable point and to generate a zoom image by expanding an image of the area of interest.

(B5)
The apparatus according to (B4), in which the zoom image generation section generates a zoom image by expanding an image of the area of interest with magnification determined depending on a distance from the surgical instrument to the remarkable point.

(B6)
The apparatus according to (B4) further including: an image superposition section configured to superpose the generated zoom image on an image obtained by the imaging section.

(B7)
The apparatus according to (B6), in which the image superposition section disposes the zoom image at a position at which the zoom image is overlapped with neither of the surgical instrument and the area of interest in the image.

(B8)
The apparatus according to (B6) or (B7), in which the image superposition section disposes the zoom image on any one of four corners of the image obtained by the imaging section.

(B9)
The apparatus according to any one of (B6) to (B8), in which the image superposition section also displays the estimated remarkable point.

(B10)
The apparatus according to (B9), in which the image superposition section displays the extension line obtained by extending a line segment corresponding to the three-dimensional position of the surgical instrument, along with the remarkable point.

(B11) The apparatus according to any one of (B6) to (B10), in which the image superposition section also displays a frame for indicating the area of interest.

(B12)
The apparatus according to any one of (B6) to (B11), in which the image superposition section performs a predetermined color conversion process on the image or the zoom image and superposes the image or the zoom image subjected to the color conversion process on each other.

(B13)
The apparatus according to any one of (B6) to (B12), in which the image superposition section superposes the zoom image on the image when a superposition mode is ON.

(B14)
The apparatus according to any one of (B1) to (B13), in which the position detection section detects the three-dimensional position of the surgical instrument by generating a parallax image from the plurality of images and detecting a linear edge in the parallax image.

(B15)
The apparatus according to any one of (B1) to (B13), in which the position detection section detects the three-dimensional position of the surgical instrument by detecting a mark which is marked on the surgical instrument.

(B16)
The apparatus according to any one of (B1) to (B15) further including: a depth information generation section configured to generate the depth information of the plurality of images calculated from the images, in which the position detection section obtains the depth information of the images generated in the depth information generation section.

(B17)
An image processing method for causing the image processing apparatus to obtain depth information of a plurality of images calculated from the images which are obtained by a plurality of imaging sections imaging a surgery region being a region of a surgical target and to detect a three-dimensional position of a surgical instrument in the image by using the obtained depth information of the images.

It should be understood by those skilled in the art that various modifications, combinations, sub-combinations and alterations may occur depending on design requirements and other factors insofar as they are within the scope of the appended claims or the equivalents thereof.

REFERENCE SIGNS LIST

11 Endoscope Camera head
12 CCU
13 Operation section
14 Display
21 Imaging section
24a First imaging sensor
24b Second imaging sensor
41 Depth information generation section
42 Forceps/area position detection section
43 Remarkable point estimation section
44 Zoom image generation section
45 Image superposition section
46 Operation control section
61 Foot pedal
Q Remarkable point
QA Area of interest
111 Guide line
QB Zoom image
201 CPU 202 ROM
203 RAM
206 Input section
207 Output section
208 Storage section
209 Communication section
210 Drive

The invention claimed is:

1. A medical imaging apparatus, comprising:
circuitry configured to:
control display on a display area of a medical image,
detect a position of an important element within the medical image,
estimate a remarkable point in the medical image in accordance with the important element,
determine a region of interest portion of the medical image, wherein the region of interest portion of the medical image includes the remarkable point and excludes the important element,
control display on the display area of a superimposed image corresponding to the medical image such that the superimposed image is displayed overlapped on the medical image, and
determine a position of the superimposed image within the display area, based on the detected position of the important element, such that the superimposed image does not overlap on the important element within the medical image, wherein the superimposed image is a zoomed image corresponding to the region of interest portion of the medical image.

2. The medical imaging apparatus according to claim 1, wherein the circuitry is further configured to detect an overlap between a portion of the important element and a portion of the superimposed image within the display area and adjust, in response to the overlap being detected, the position of the superimposed image within the display area such that superimposed image is no longer overlapping on the portion of the important element within the medical image.

3. The medical imaging apparatus according to claim 1, wherein the medical image includes a surgical image of a body.

4. The medical imaging apparatus according to claim 1, wherein the important element is an important object or an important area.

5. The medical imaging apparatus according to claim 1, wherein the superimposed image corresponds to the region of interest portion of the medical image and the region of interest portion is estimated from a three-dimensional posture of the important element.

6. The medical imaging apparatus according to claim 1, wherein the important element is a surgical instrument.

7. The medical imaging apparatus according to claim 1, wherein the circuitry is further configured to:
detect a second position of the important element within the medical image after a movement of the important element within the medical image,
detect a second overlap between the detected second position of the important element and the adjusted position of the superimposed image, and
further adjust, in response to the second overlap being detected, the adjusted position of the superimposed image within the display area such that the superimposed image is no longer overlapping on the detected second position of the important element within the medical image.

8. The medical imaging apparatus according to claim 1, wherein the circuitry is configured to control display on the display area of a frame indicating the region of interest portion.

9. The medical imaging apparatus according to claim 1, wherein the superimposed image is positioned in any one of four corners of the medical image.

10. The medical imaging apparatus according to claim 1, wherein the superimposed image is subjected to a color conversion process.

11. A method for processing a medical image by a medical imaging apparatus including circuitry, the method comprising:
controlling display on a display area of a medical image,
detecting, by the circuitry, a position of an important element within the medical image,
estimating, by the circuitry, a remarkable point in the medical image in accordance with the important element,
determining, by the circuitry, a region of interest portion of the medical image, wherein the region of interest portion of the medical image includes the remarkable point and excludes the important element,
controlling display on the display area of a superimposed image corresponding to the medical image such that the superimposed image is displayed overlapped on the medical image, and
determining a position of the superimposed image within the display area, based on the detected position of the important element, such that the superimposed image does not overlap on the important element within the medical image, wherein the superimposed image is a zoomed image corresponding to the region of interest portion of the medical image.

12. A non-transitory computer readable medium having stored thereon a program that when executed by a computer causes the computer to implement a method for processing a medical image by a medical imaging apparatus including circuitry, the method comprising:
controlling display on a display area of a medical image;
detecting, by the circuitry, a position of an important element within the medical image,
estimating, by the circuitry, a remarkable point in the medical image in accordance with the important element,
determining, by the circuitry, a region of interest portion of the medical image, wherein the region of interest portion of the medical image includes the remarkable point and excludes the important element,
controlling display on the display area of a superimposed image corresponding to the medical image such that the superimposed image is displayed overlapped on the medical image; and
determining a position of the superimposed image within the display area, based on the detected position of the important element, such that the superimposed image does not overlap on the important element within the medical image, wherein the superimposed image is a zoomed image corresponding to the region of interest portion of the medical image.

13. A medical imaging system, comprising:
a medical imaging device that obtains a medical image;
a display device having a display area; and
circuitry configured to:
control display on the display area of the display device of the medical image obtained by the medical imaging device, detect a position of an important element within the medical image, estimate a remarkable point in the medical image in accordance with the important element, determine a region of interest portion of the medical image, wherein the region of interest portion of the medical image includes the remarkable point and excludes the important element, control display on the display area of the display device of a superimposed image corresponding to the medical image such that the superimposed image is displayed overlapped on the medical image, and determine a position of the superimposed image within the display area, based on the detected position of the important element, such that the superimposed image does not overlap on the important element within the medical image, wherein the superimposed image is a zoomed image corresponding to the region of interest portion of the medical image.

14. The system according to claim 13, wherein the medical imaging device is an endoscope or a surgical microscope.

* * * * *